US011352391B2

(12) United States Patent
Ricca et al.

(10) Patent No.: US 11,352,391 B2
(45) Date of Patent: Jun. 7, 2022

(54) COMPOSITIONS FOR INDUCING URINARY VOIDING AND DEFECATION

(71) Applicant: Dignify Therapeutics, LLC, Research Triangle Park, NC (US)

(72) Inventors: Daniel Joseph Ricca, Research Triangle Park, NC (US); Edward C. Burgard, Research Triangle Park, NC (US)

(73) Assignee: DIGNIFY THERAPEUTICS, LLC, Research Triangle Park, NC (US)

( * ) Notice: Subject to any disclaimer, the term of this patent is extended or adjusted under 35 U.S.C. 154(b) by 29 days.

(21) Appl. No.: 16/647,926

(22) PCT Filed: Mar. 21, 2018

(86) PCT No.: PCT/US2018/023466
§ 371 (c)(1),
(2) Date: Mar. 17, 2020

(87) PCT Pub. No.: WO2019/059963
PCT Pub. Date: Mar. 28, 2019

(65) Prior Publication Data
US 2020/0262868 A1 Aug. 20, 2020

Related U.S. Application Data

(60) Provisional application No. 62/561,387, filed on Sep. 21, 2017.

(51) Int. Cl.
| *C07K 7/06* | (2006.01) |
| *A61K 38/08* | (2019.01) |
| *A61P 1/10* | (2006.01) |
| *A61P 13/00* | (2006.01) |
| *A61K 9/00* | (2006.01) |

(52) U.S. Cl.
CPC .............. *C07K 7/06* (2013.01); *A61K 9/0053* (2013.01); *A61K 38/08* (2013.01); *A61P 1/10* (2018.01); *A61P 13/00* (2018.01)

(58) Field of Classification Search
CPC ... C07K 7/06; A61K 38/03; A61P 1/10; A61P 13/00
See application file for complete search history.

(56) References Cited

U.S. PATENT DOCUMENTS

| 10,086,034 B2 * | 10/2018 | Thor ...................... A61K 45/06 |
| 2012/0156279 A1 | 6/2012 | Yu et al. |
| 2016/0175382 A1 * | 6/2016 | Thor ......................... A61P 1/00 |
| | | 514/21.7 |

FOREIGN PATENT DOCUMENTS

| EP | 0401177 A1 | 12/1990 |
| WO | 2014061772 A1 | 4/2014 |

OTHER PUBLICATIONS

Mant et al. "HPLC Analysis and Purification of Peptides", Peptide Characterization and Application Protocols, 2007, pp. 3-55 (Year: 2007).*
Evangelista et al. "Analogs of Neurokinin A(4-10) Afford Protection Against Gastroduodenal Ulcers in Rats", Peptides, pp. 293-297, 1990 (Year: 1990).*
Sagan et al. "Tachykinin Peptides Affect Differently the Second Messenger Pathways after Binding to CHO-Expressed Human NK-1 Receptors", The Journal of Pharmacology and Experimental Therapeutics, 1995, pp. 1039-1048 (Year: 1995).*
Warner et al. "Structure-activity relationship of neurokinin A (4-10) at the human tachykinin NK2 receptor: the effect of amino acid substitutions on receptor affinity and function", Biochemical Pharmacology, 2002, pp. 2181-2186 (Year: 2002).*
ISA/US; International Search Report and Written Opinion for International Patent Application No. PCT/US2018/023466 dated Jul. 20, 2018, 13 pages.
Kullman, Fa et al., "Pharmacodynamic evaluation of Lys5, MeLeu9, Nle10-NKA(4-10) prokinetic effects on bladder and colon activity in acute spinal cord transected and spinally intact rats", Naunyn-Schmiedeberg's Archives of Pharmacology, Feb. 2017, vol. 390, No. 2, pp. 163-173.
WIPO; International Preliminary Report on Patentability for International Patent Application No. PCT/US2018/023466 dated Apr. 2, 2020, 9 pages.

* cited by examiner

*Primary Examiner* — Lianko G Garyu
(74) *Attorney, Agent, or Firm* — NK Patent Law

(57) ABSTRACT

Eleven synthetic neurokinin A peptide analogs are provided as therapeutic compounds for inducing voluntary "on-demand" voiding of urine and feces in mammals who cannot void without external invasion of the bladder and bowel or those who void involuntarily (i.e., those having urinary and/or fecal incontinence). This control over when and where individuals void offers a drastic improvement in quality of life.

19 Claims, 24 Drawing Sheets

Specification includes a Sequence Listing.

SEQUENCE LISTING

```
<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(6)
<223> OTHER INFORMATION: Leu at position 6 is methylated at the nitrogen
<220> FEATURE:
<221> NAME/KEY: MISC_FEATURE
<222> LOCATION: (7)..(7)
<223> OTHER INFORMATION: Met at position 7 has a NH2 group at the
      carboxyl terminus
```

```
<400> SEQUENCE: 1

Asp Lys Phe Val Gly Leu Met
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(6)
<223> OTHER INFORMATION: Leu at position 6 is methylated at the nitrogen
<220> FEATURE:
<221> NAME/KEY: MISC_FEATURE
<222> LOCATION: (7)..(7)
<223> OTHER INFORMATION: X at position 7 is norleucine
<220> FEATURE:
<221> NAME/KEY: MISC_FEATURE
<222> LOCATION: (7)..(7)
<223> OTHER INFORMATION: X at position 7 is norleucine that has a NH2
      group at the carboxy terminus

<400> SEQUENCE: 2

Asp Arg Phe Val Gly Leu Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(6)
<223> OTHER INFORMATION: Leu at position 6 is methylated at the nitrogen
<220> FEATURE:
<221> NAME/KEY: MISC_FEATURE
<222> LOCATION: (7)..(7)
<223> OTHER INFORMATION: Met at position 7 has a NH2 group at the
      carboxyl terminus

<400> SEQUENCE: 3

Asp Arg Phe Val Gly Leu Met
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(7)
<223> OTHER INFORMATION: Met at position 7 has a NH2 group at the
      carboxyl terminus

<400> SEQUENCE: 4

Asp Lys Phe Val Gly Leu Met
1               5

<210> SEQ ID NO 5
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: Ala at position 5 is beta Ala
<220> FEATURE:
<221> NAME/KEY: MISC_FEATURE
<222> LOCATION: (7)..(7)
<223> OTHER INFORMATION: Met at position 7 has a NH2 group at the
      carboxyl terminus

<400> SEQUENCE: 5

Asp Lys Phe Val Ala Leu Met
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(7)
<223> OTHER INFORMATION: X at position 7 is a norleucine that has a NH2
      group at the carboxyl terminus

<400> SEQUENCE: 6

Asp Lys Phe Val Gly Leu Xaa
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: Ala at position 5 is beta Ala
<220> FEATURE:
<221> NAME/KEY: MISC_FEATURE
<222> LOCATION: (7)..(7)
<223> OTHER INFORMATION: X at position 7 is norleucine that has a NH2
      group at the carboxyl terminus

<400> SEQUENCE: 7

Asp Lys Phe Val Ala Leu Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(7)
<223> OTHER INFORMATION: Met at position 7 has a NH2 group at the
      carboxyl terminus

<400> SEQUENCE: 8

Asp Arg Phe Val Gly Leu Met
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: Ala at position 5 is beta Ala
<220> FEATURE:
<221> NAME/KEY: MISC_FEATURE
<222> LOCATION: (7)..(7)
<223> OTHER INFORMATION: Met at position 7 has a NH2 group at the
      carboxyl terminus

<400> SEQUENCE: 9

Asp Arg Phe Val Ala Leu Met
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(7)
<223> OTHER INFORMATION: X at position 7 is a norleucine that has a NH2
      group at the carboxyl terminus

<400> SEQUENCE: 10

Asp Arg Phe Val Gly Leu Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: Ala at position 5 is beta Ala
<220> FEATURE:
<221> NAME/KEY: MISC_FEATURE
<222> LOCATION: (7)..(7)
<223> OTHER INFORMATION: X at position 7 is a norleucine that has a NH2
      group at the carboxyl terminus

<400> SEQUENCE: 11

Asp Arg Phe Val Ala Leu Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
```

```
<222> LOCATION: (5)..(5)
<223> OTHER INFORMATION: Gly or betaAla
<220> FEATURE:
<221> NAME/KEY: MOD_RES
<222> LOCATION: (6)..(6)
<223> OTHER INFORMATION: Leu or NMe-Leu
<220> FEATURE:
<221> NAME/KEY: MOD_RES
<222> LOCATION: (7)..(7)
<223> OTHER INFORMATION: Met or Nle
<220> FEATURE:
<223> OTHER INFORMATION: C term NH2

<400> SEQUENCE: 12

Asp Xaa Phe Val Xaa Xaa Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: BetaAla
<220> FEATURE:
<221> NAME/KEY: MOD_RES
<222> LOCATION: (6)..(6)
<223> OTHER INFORMATION: NMe-Leu
<220> FEATURE:
<223> OTHER INFORMATION: C term NH2

<400> SEQUENCE: 13

Asp Lys Phe Val Ala Leu Met
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: NMe-Leu
<220> FEATURE:
<221> NAME/KEY: MOD_RES
<222> LOCATION: (7)..(7)
<223> OTHER INFORMATION: Nle
<220> FEATURE:
<223> OTHER INFORMATION: C term NH2

<400> SEQUENCE: 14

Asp Lys Phe Val Gly Leu Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: BetaAla
<220> FEATURE:
```

```
<221> NAME/KEY: MOD_RES
<222> LOCATION: (6)..(6)
<223> OTHER INFORMATION: NMe-Leu
<220> FEATURE:
<223> OTHER INFORMATION: C term NH2

<400> SEQUENCE: 15

Asp Arg Phe Val Ala Leu Met
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: BetaAla
<220> FEATURE:
<221> NAME/KEY: MOD_RES
<222> LOCATION: (6)..(6)
<223> OTHER INFORMATION: NMe-Leu
<220> FEATURE:
<221> NAME/KEY: MOD_RES
<222> LOCATION: (7)..(7)
<223> OTHER INFORMATION: Nle
<220> FEATURE:
<223> OTHER INFORMATION: C term NH2

<400> SEQUENCE: 16

Asp Lys Phe Val Ala Leu Leu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: BetaAla
<220> FEATURE:
<221> NAME/KEY: MOD_RES
<222> LOCATION: (6)..(6)
<223> OTHER INFORMATION: NMe-Leu
<220> FEATURE:
<221> NAME/KEY: MOD_RES
<222> LOCATION: (7)..(7)
<223> OTHER INFORMATION: Nle
<220> FEATURE:
<223> OTHER INFORMATION: C term NH2

<400> SEQUENCE: 17

Asp Arg Phe Val Ala Leu Leu
1               5
```

COMPOSITIONS FOR INDUCING URINARY VOIDING AND DEFECATION

CROSS REFERENCE TO RELATED APPLICATIONS

The present application is a U.S. National Stage Application of International Patent Application No. PCT/US18/23466, filed on Mar. 21, 2018, which claims the benefit under 35 U.S.C. § 119(e) of U.S. Provisional Patent Application Ser. No. 62/561,387 filed on Sep. 21, 2017, the entire contents of which are all incorporated herein by reference.

SEQUENCE LISTING

The instant application contains a Sequence Listing which has been submitted electronically in ASCII format and is hereby incorporated by reference in its entirety. Said ASCII copy, created on Mar. 4, 2021, is named 336_9_UTIL_SL.txt and is 7,055 bytes in size.

TECHNICAL FIELD

The presently disclosed subject matter relates to compositions for inducing urinary voiding and defecation.

BACKGROUND

The inability to eliminate urine and/or feces is a life-threatening condition. The current standard of care for severe urinary retention requires passage of a clean catheter through the urethra and further into the urinary bladder to facilitate urine flow through the catheter externally. The current standard of care for severe fecal impaction includes digital extraction of feces from the rectum in combination with a diet conducive to stool passage. Some patients receive large volume (1 L) warm water enemas or stimulant suppositories that can require waiting for 30 minutes to an hour while fecal contents are expelled. The lack of control over urination and defecation substantially impairs quality of life for both patients and caregivers and is a leading cause of institutionalization (Lee et al, 2016).

Voiding dysfunction is extremely prevalent in patients with spinal cord injury, spina bifida, multiple sclerosis, and other conditions involving spinal cord pathology. Voiding dysfunction is also prevalent in subjects with diabetic cystopathy and gastroenteropathy. Voiding dysfunction is also seen in various elderly subjects and is prevalent among the institutionalized.

Existing therapies for urinary retention include either clean intermittent or indwelling catheterization which can result in catheter associated urinary tract infections (CAUTI). CAUTI account for more than 15% of infections reported by acute care hospitals and can lead to complications such as cystitis, pyelonephritis, gram-negative bacteremia, prostatitis, epididymitis, and orchitis in males and, less commonly, endocarditis, vertebral osteomyelitis, septic arthritis, endophthalmitis, and meningitis in all patients. Complications associated with CAUTI cause discomfort to the patient, prolong hospital stay, and increase cost and mortality. Each year, more than 13,000 deaths are associated with UTIs. In addition, persons with SCI (and other CNS damage) often lack the physical ability to catheterize themselves.

Cholinergic agonists such as bethanechol (a muscarinic receptor agonist) and distigmine (an acetylcholinesterase inhibitor) have been used as therapy to treat urinary retention. However, the efficacy of these compounds is limited and tolerability is low due to severe side effects such as sweating, spasticity, bradycardia, convulsions, hypotension, and bronchial constriction. Alternative methods have been developed to empty the bladder by preventing the sphincter from closing the urethra, but most of them, including sphincterotomy, sphincter paralysis, and urethral stenting, leave the person incontinent and lead to further complications.

Lower urinary tract disorders including underactive bladder and incontinence greatly affect the quality of life of patients. Voiding dysfunction associated with the inability to completely void the bladder of urine during micturition is a condition affecting the elderly, diabetic, neurogenic (spinal cord injury, spina bifida, multiple sclerosis, stroke patients, traumatic brain injury, Parkinson's, Alzheimer's, ALS), and other patient populations. The condition can arise from impaired contractility of the bladder smooth muscle of myogenic nature, e.g. in the elderly; impaired relaxation of the urethral smooth muscle, e.g. in the elderly; damage of the peripheral nerves (afferents and/or efferents) e.g. in diabetic neuropathy; impaired neuronal control due to injury of the spinal cord or brain, e.g. in spinal cord injury, multiple sclerosis, stroke patients, traumatic brain injury, Parkinson's, Alzheimer's, and other conditions and disorders. This condition can lead to elevated post-void residual urine volumes and symptoms of frequency, nocturia, incontinence, and urinary tract infections.

Spinal cord injury is the most common injury that profoundly affects voiding and usually results from traffic accidents, sports injuries, but also from infections, vascular disorders, cancers, congenital malformations, polio, tuberculosis, etc. It is estimated that the annual incidence of spinal cord injury (SCI), not including those who die at the scene of the accident, is approximately 40 cases per million population in the U. S. or approximately 12,000 new cases each year. The number of people in the United States who are alive in 2012 who have SCI has been estimated to be approximately 270,000 persons, with a range of 236,000 to 327,000 persons.

For a person with SCI, the direct medical costs associated with urinary tract dysfunction may exceed $8,000 each year, making up a substantial component of the estimated $31,000 to $75,000 annual health care and living expenses of individuals with spinal injury. Furthermore, the loss of control of urinary function alters social relationships and can be personally demoralizing, and it can lead to depression, anger, poor self-image, embarrassment, frustration and can prevent persons from achieving their personal goals.

Urinary sphincter muscles may also be affected by spinal cord injuries, resulting in a condition known as "dyssynergia." Dyssynergia involves an inability of urinary sphincter muscles to relax when the bladder contracts, including active contraction in response to bladder contraction, which prevents urine from flowing through the urethra and results in the incomplete emptying of the bladder and "reflux" of urine into the kidneys. Traditional treatments for dyssynergia include medications that have been somewhat inconsistent in their efficacy or surgery.

Injury to spinal cord and/or brain can lead to an inability to voluntarily defecate and subsequent fecal impaction. Currently patients use digital rectal stimulation and manual extraction of feces, or in some cases use large volume (1 L) warm water enemas that require sitting on the toilet for 30 minutes to an hour while the water and fecal contents are expelled. In some cases, an irritative "stimulant laxative" is administered intra-rectally, although effects may last hours longer than necessary and cannot be administered on a regular basis. These methods are either performed by the patient, if able to perform them, or by the caregiver. They can be degrading to the self-esteem of patients and can be personally demoralizing and stigmatizing, altering social relationships, leading to depression, anger, poor self-image, embarrassment, frustration, etc.

Incontinence, fecal impaction, and urinary retention demand diligent personal care. Repeated catheterization to empty the bladder may cause urinary tract infection and other complications requiring further interventions (Singh et al. 2011; Yilmaz et al. 2014). Relief from fecal impaction typically requires enemas and manual extraction (Hughes 2014). A drug therapy that could be used to facilitate micturition and defecation on-demand would greatly improve the quality of care; however, this remains a largely neglected unmet medical need (van Koeveringe et al, 2011.

Because existing therapies and treatments for voiding dysfunction are associated with limitations as described above, new therapies and treatments are therefore desirable. The presently disclosed subject matter provides such new therapies and treatments to address these limitations.

SUMMARY

In one embodiment of the presently disclosed subject matter, a synthetic peptide is provided selected from the group consisting of an amino acid sequence: Asp-Lys-Phe-Val-Gly-(NMe-Leu)-Met-NH2 (SEQ ID NO: 1), Asp-Arg-Phe-Val-Gly-(NMe-Leu)-Nle-NH2 (SEQ ID NO: 2), Asp-Arg-Phe-Val-Gly-(NMe-Leu)-Met-NH2 (SEQ ID NO: 3), Asp-Lys-Phe-Val-Gly-Leu-Met-NH2 (SEQ ID NO: 4), Asp-Lys-Phe-Val-(β-Ala)-Leu-Met-NH2 (SEQ ID NO: 5), Asp-Lys-Phe-Val-Gly-Leu-Nle-NH2 (SEQ ID NO: 6), Asp-Lys-Phe-Val-(β-Ala)-Leu-Nle-NH2 (SEQ ID NO: 7), Asp-Arg-Phe-Val-Gly-Leu-Met-NH2 (SEQ ID NO: 8), Asp-Arg-Phe-Val-(β-Ala)-Leu-Met-NH2 (SEQ ID NO: 9), Asp-Arg-Phe-Val-Gly-Leu-Nle-NH2 (SEQ ID NO: 10), and Asp-Arg-Phe-Val-(β-Ala)-Leu-Nle-NH2 (SEQ ID NO: 11).

In one embodiment of the presently disclosed subject matter, a pharmaceutical composition is provided comprising a peptide selected from the group consisting of SEQ ID NOs: 1-11, or a pharmaceutically acceptable salt thereof, and a pharmaceutically acceptable excipient.

In one embodiment of the presently disclosed subject matter, a pharmaceutical composition is provided comprising a peptide selected from the group consisting of SEQ ID NOs: 1-3, or a pharmaceutically acceptable salt thereof, in a formulation beneficial for a hydrophilic active ingredient.

In one embodiment of the presently disclosed subject matter, a pharmaceutical composition is provided comprising a peptide selected from the group consisting of SEQ ID NOs: 5, 7, and 11, or a pharmaceutically acceptable salt thereof, in a formulation beneficial for a hydrophobic active ingredient.

In one embodiment of the presently disclosed subject matter, a pharmaceutical composition is provided comprising a peptide selected from the group consisting of SEQ ID NOs: 1, 2, 7, and 11, or a pharmaceutically acceptable salt thereof, and a pharmaceutically acceptable excipient.

In one embodiment of the presently disclosed subject matter, a method is provided for inducing one or both of urinary voiding and defecation in a mammal, which comprises administering on an as-needed basis to the mammal a therapeutically effective amount of a composition comprising a peptide selected from the group consisting of SEQ ID NOs: 1-11, or a pharmaceutically acceptable salt thereof, and a pharmaceutically acceptable excipient, to induce the as-needed one or both of urinary voiding and defecation. The composition can be formulated as an immediate release dosage form. The administering can be one or a combination of parenteral, intravenous, topical, transdermal, intramuscular, subcutaneous, transnasal, inhalation, transrectal, lingual, sublingual, transmucosal, and transbuccal. The administering can be lingual in the form of a rapidly disintegrating tablet. The one of voiding and defecation dysfunction is a result of one of spinal cord injury, traumatic brain injury, multiple sclerosis, spina bifida, degenerative brain disease, Alzheimer's, Parkinson's, dementia, diabetes, advanced age, postoperative status, and combinations thereof. The mammal can be a human, an animal, a cat, a dog, a horse, a cow, a pig, or a sheep. The as-needed administering can range from about 1 minute to about 5 minutes prior to when the voiding and/or defecation is desired. The as-needed administering can range from about 1 minute to about 10 minutes prior to when the voiding and/or defecation is desired. The as-needed administering can be repeated multiple times per day.

In one embodiment of the presently disclosed subject matter, a method is provided for preparing a peptide selected from the group consisting of SEQ ID NOs: 1-11, the method comprising: chemically synthesizing a peptide comprising the amino acid sequence of a peptide selected from the group consisting of SEQ ID NOs: 1-11; and purifying the peptide.

BRIEF DESCRIPTION OF THE FIGURES

The foregoing aspects and other features of the invention are explained in the following description, taken in connection with the accompanying drawings.

FIG. 3.

FIG. 3.

DETAILED DESCRIPTION

Figure 1A:
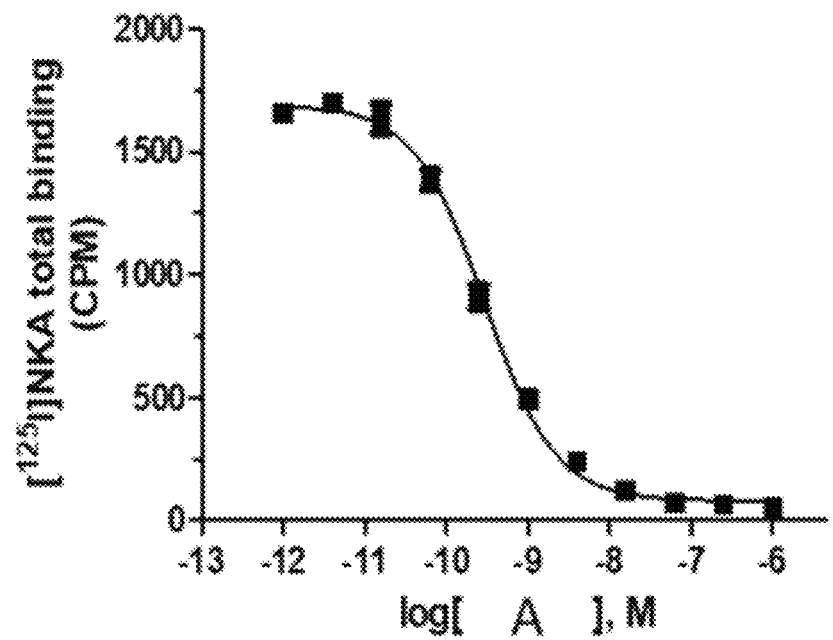
FIG. 1A is a graph of a human NK2 Receptor (hNK2R) displacement curve for heptapeptide analog A (SEQ ID NO: 1) according to one or more embodiments of the invention.
Figure 1B:
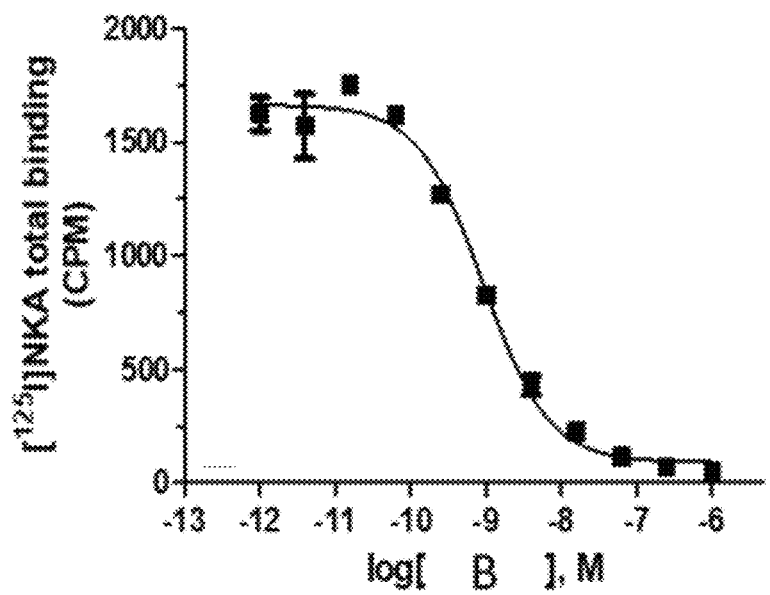
FIG. 1B is a graph of a human NK2 Receptor (hNK2R) displacement curve for heptapeptide analog B (SEQ ID NO: 2) according to one or more embodiments of the invention.
Figure 1C:
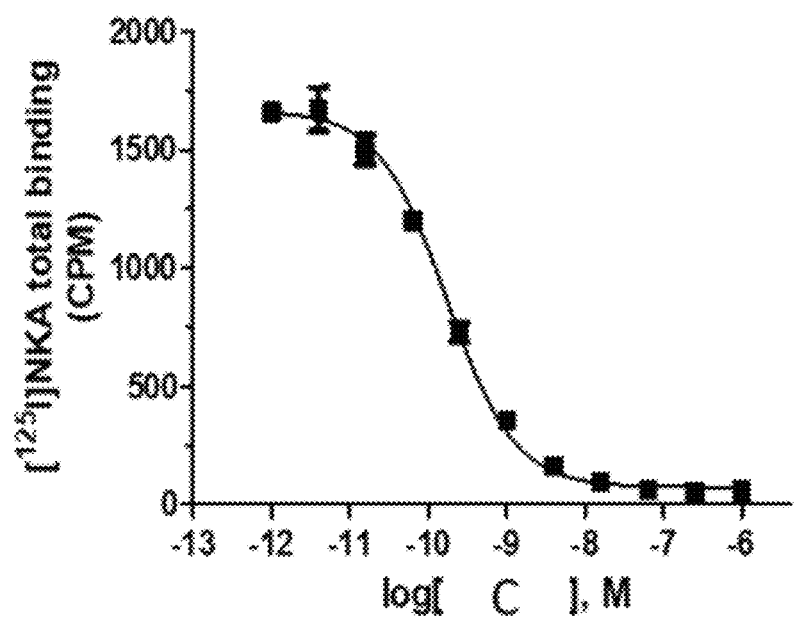
FIG. 1C is a graph of a human NK2 Receptor (hNK2R) displacement curve for heptapeptide analog C (SEQ ID NO: 3) according to one or more embodiments of the invention.
Figure 1D:
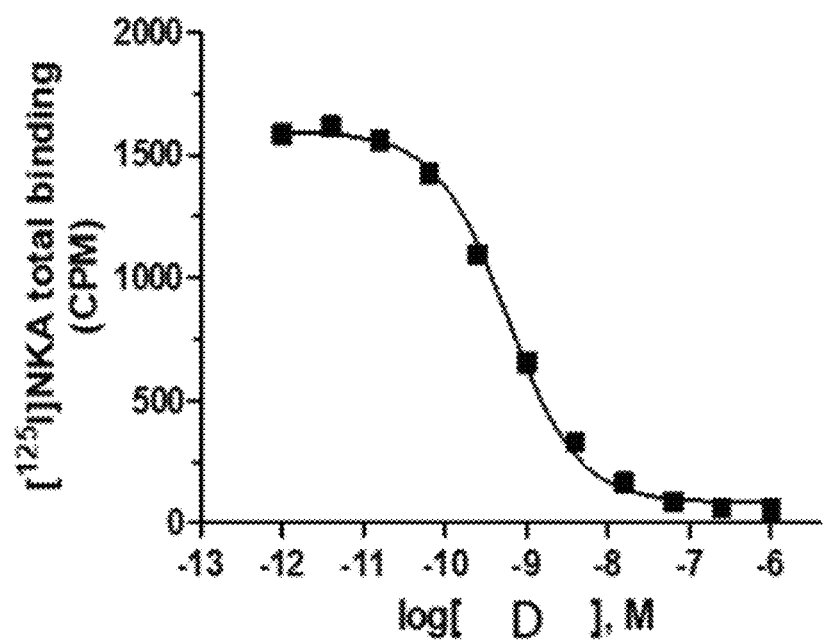
FIG. 1D is a graph of a human NK2 Receptor (hNK2R) displacement curve for heptapeptide analog D (SEQ ID NO: 4) according to one or more embodiments of the invention.
Figure 1E:
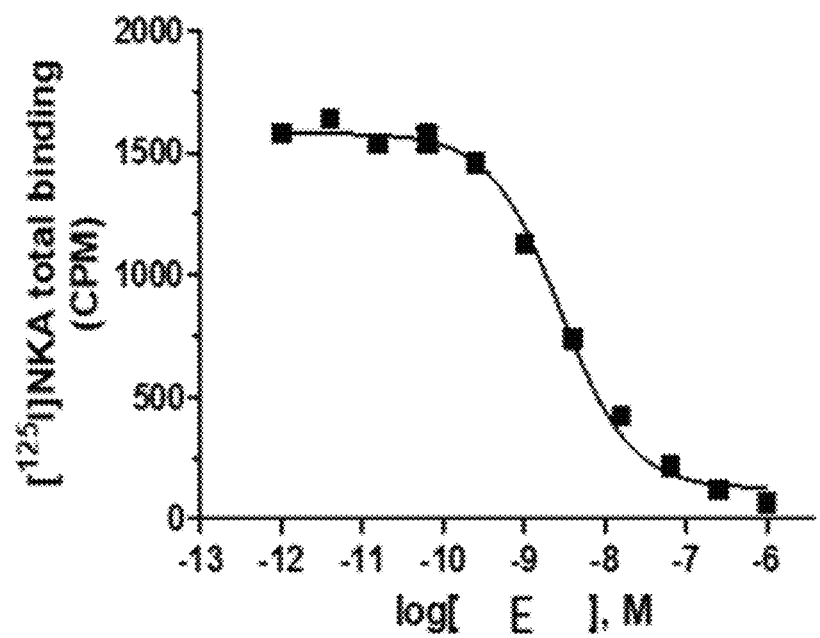
FIG. 1E is a graph of a human NK2 Receptor (hNK2R) displacement curve for heptapeptide analog E (SEQ ID NO: 5) according to one or more embodiments of the invention.
Figure 1F:
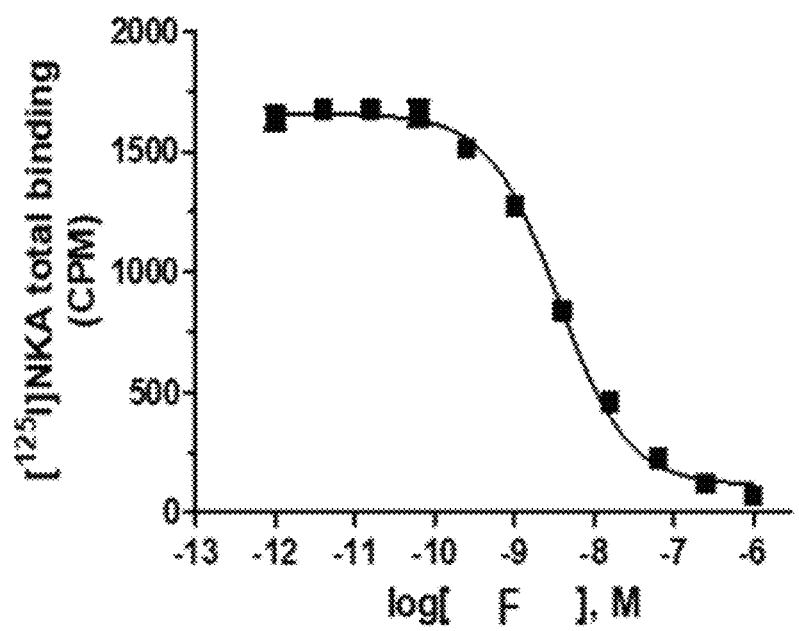
FIG. 1F is a graph of a human NK2 Receptor (hNK2R) displacement curve for heptapeptide analog F (SEQ ID NO: 6) according to one or more embodiments of the invention.
Figure 1G:
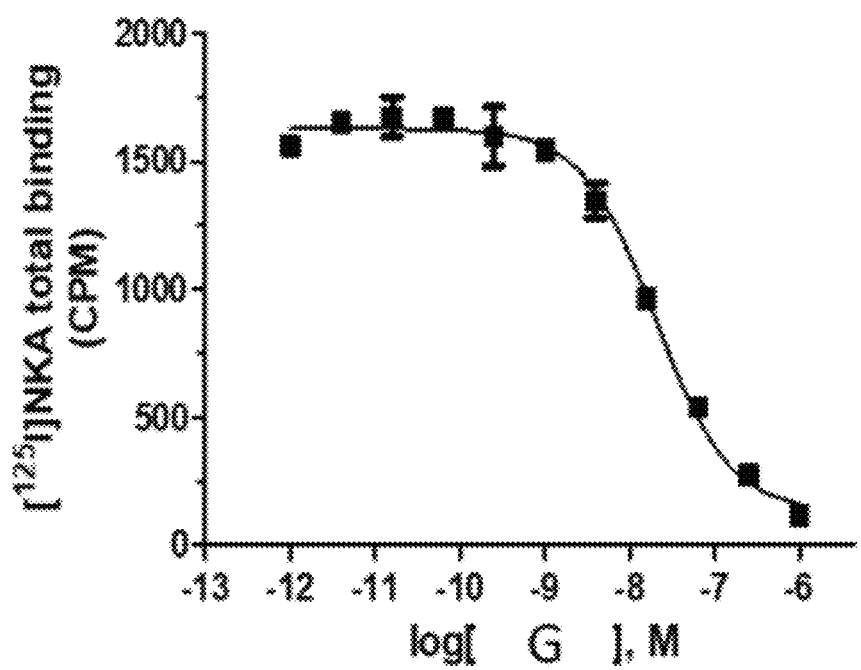
FIG. 1G is a graph of a human NK2 Receptor (hNK2R) displacement curve for heptapeptide analog G (SEQ ID NO: 7) according to one or more embodiments of the invention.
Figure 1H:
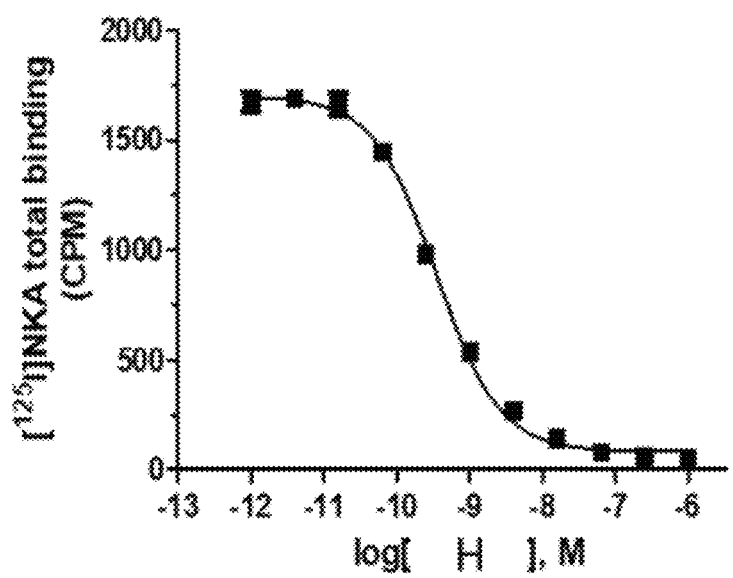
FIG. 1H is a graph of a human NK2 Receptor (hNK2R) displacement curve for heptapeptide analog H (SEQ ID NO: 8) according to one or more embodiments of the invention.
Figure 1I:
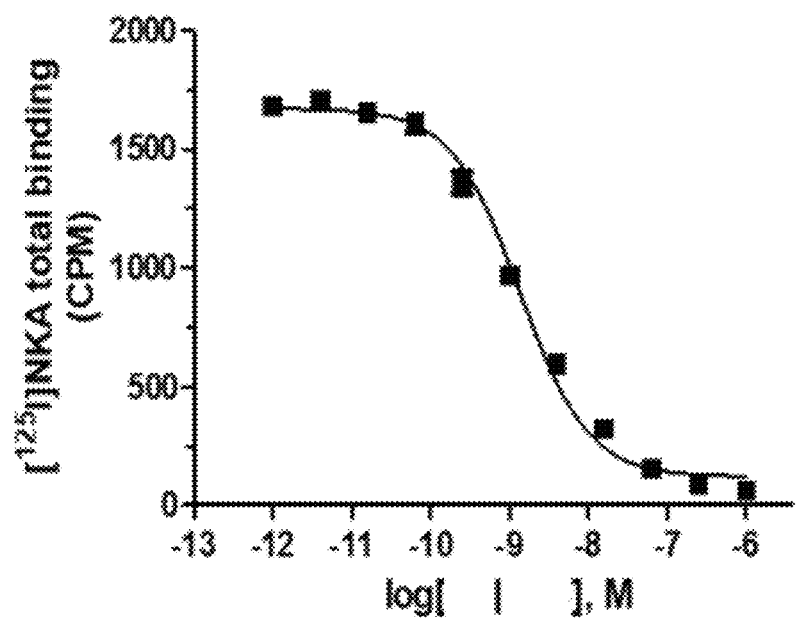
FIG. 1I is a graph of a human NK2 Receptor (hNK2R) displacement curve for heptapeptide analog I (SEQ ID NO: 9) according to one or more embodiments of the invention.
Figure 1J:
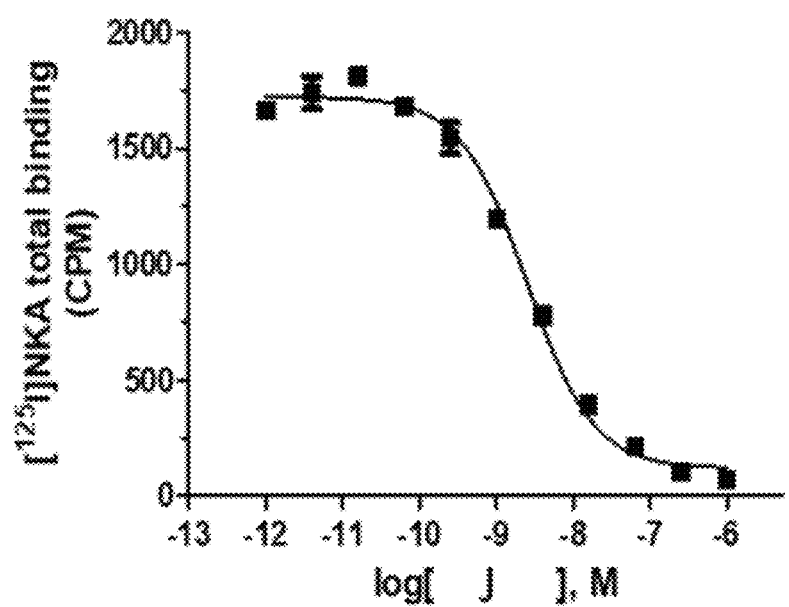
FIG. 1J is a graph of a human NK2 Receptor (hNK2R) displacement curve for heptapeptide analog J (SEQ ID NO: 10) according to one or more embodiments of the invention.
Figure 1K:
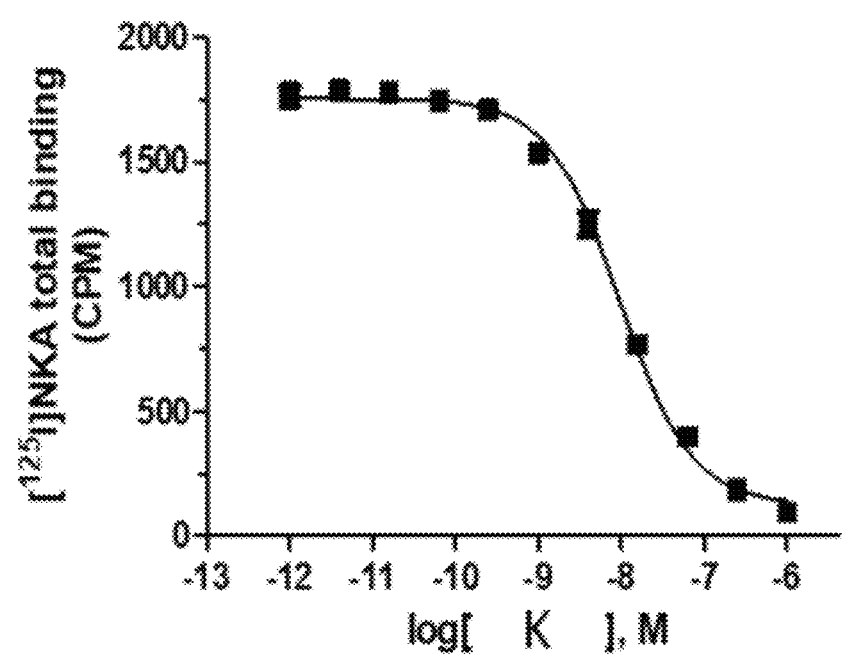
FIG. 1K is a graph of a human NK2 Receptor (hNK2R) displacement curve for heptapeptide analog K (SEQ ID NO: 11) according to one or more embodiments of the invention.
Figure 2A:
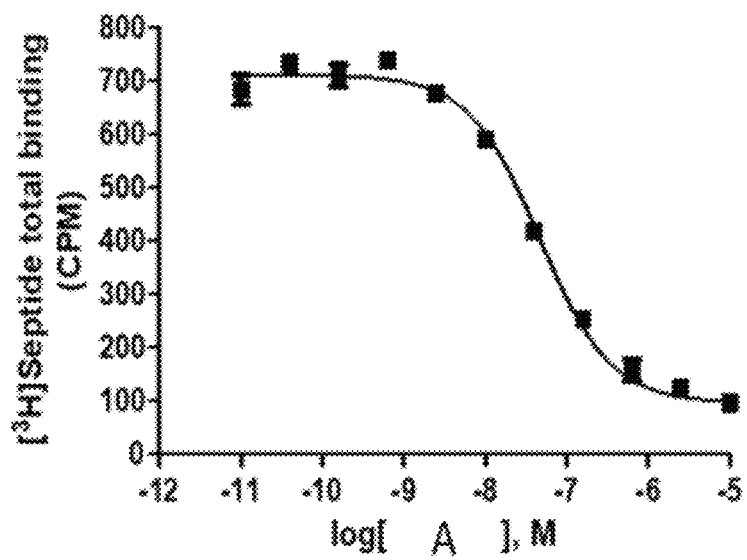
FIG. 2A is a graph of a human NK1 Receptor (hNK1R) displacement curve for heptapeptide analog A (SEQ ID NO: 1) according to one or more embodiments of the invention.
Figure 2B:
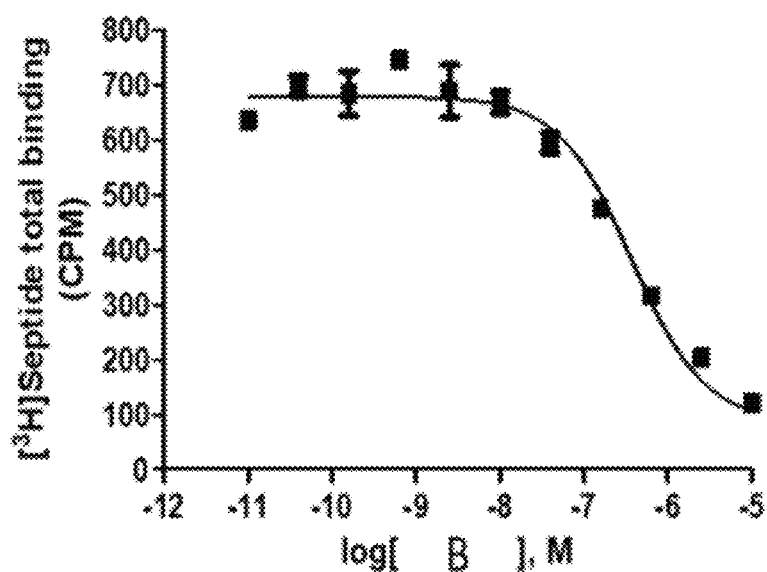
FIG. 2B is a graph of a human NK1 Receptor (hNK1R) displacement curve for heptapeptide analog B (SEQ ID NO: 2) according to one or more embodiments of the invention.
Figure 2C:
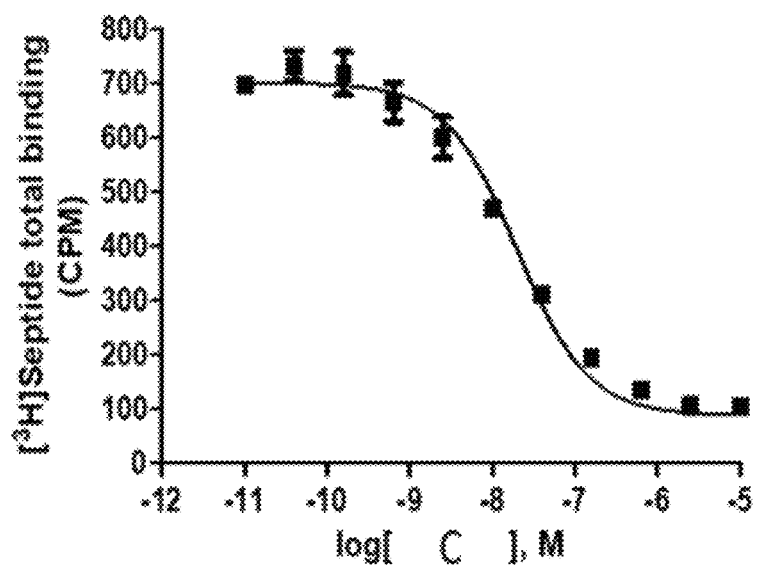
FIG. 2C is a graph of a human NK1 Receptor (hNK1R) displacement curve for heptapeptide analog C (SEQ ID NO: 3) according to one or more embodiments of the invention.
Figure 2D:
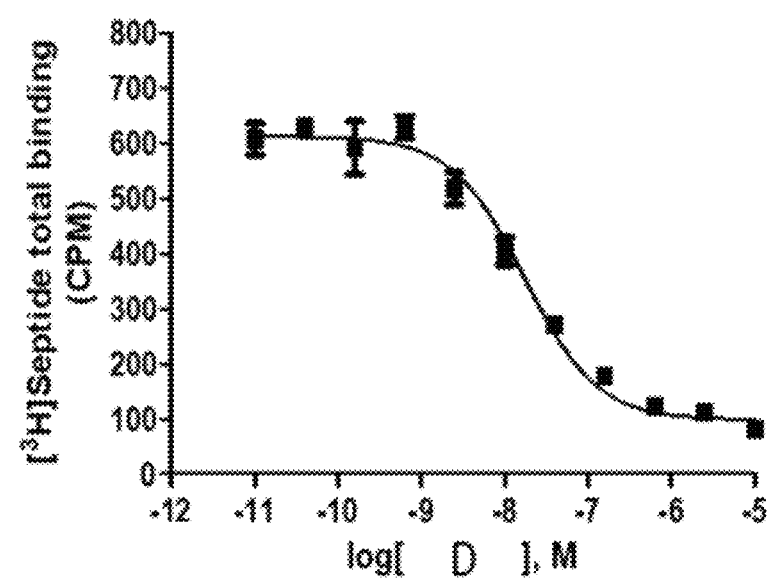
FIG. 2D is a graph of a human NK1 Receptor (hNK1R) displacement curve for heptapeptide analog D (SEQ ID NO: 4) according to one or more embodiments of the invention.
Figure 2E:
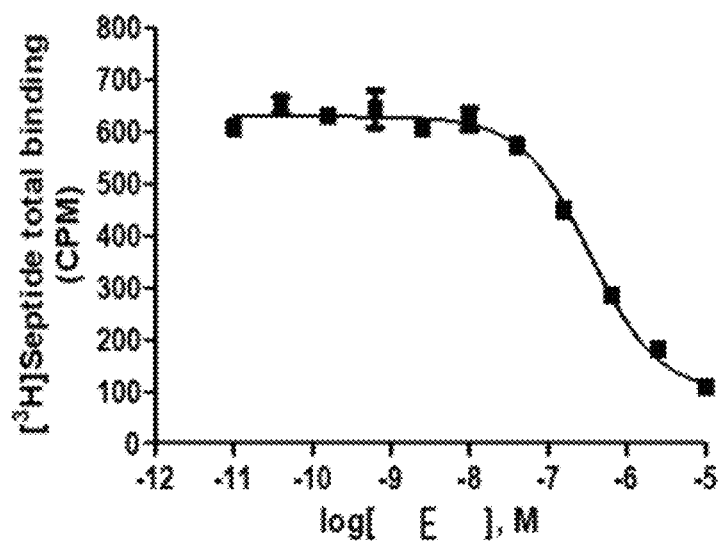
FIG. 2E is a graph of a human NK1 Receptor (hNK1R) displacement curve for heptapeptide analog E (SEQ ID NO: 5) according to one or more embodiments of the invention.
Figure 2F:
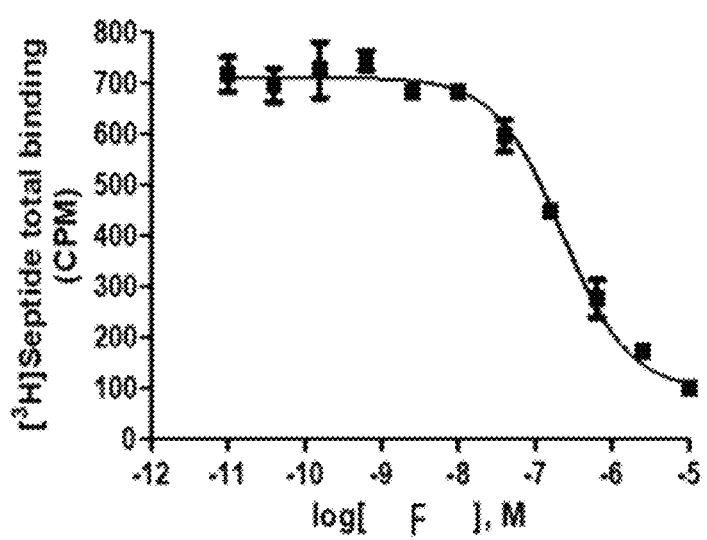
FIG. 2F is a graph of a human NK1 Receptor (hNK1R) displacement curve for heptapeptide analog F (SEQ ID NO: 6) according to one or more embodiments of the invention.
Figure 2G:
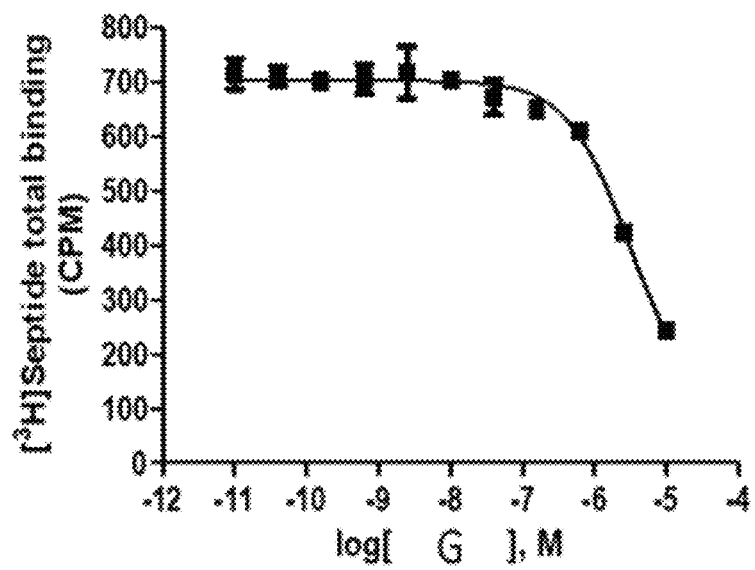
FIG. 2G is a graph of a human NK1 Receptor (hNK1R) displacement curve for heptapeptide analog G (SEQ ID NO: 7) according to one or more embodiments of the invention.
Figure 2H:
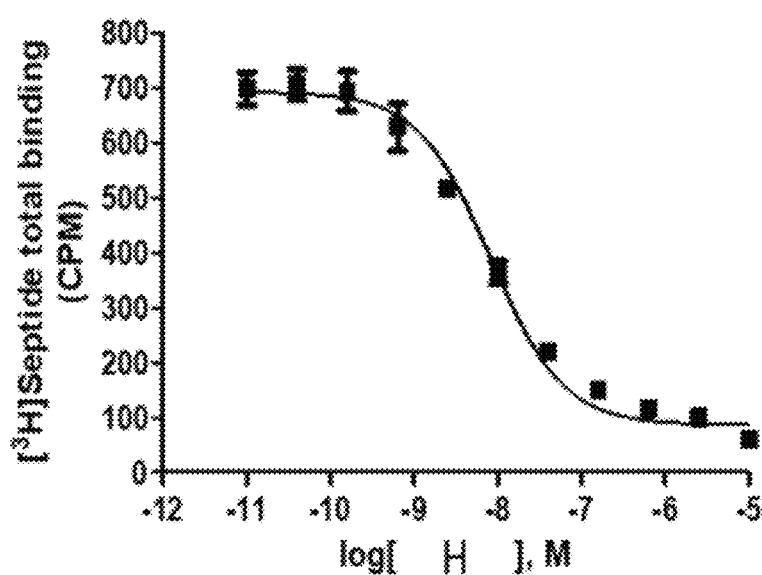
FIG. 2H is a graph of a human NK1 Receptor (hNK1R) displacement curve for heptapeptide analog H (SEQ ID NO: 8) according to one or more embodiments of the invention.
Figure 2I:
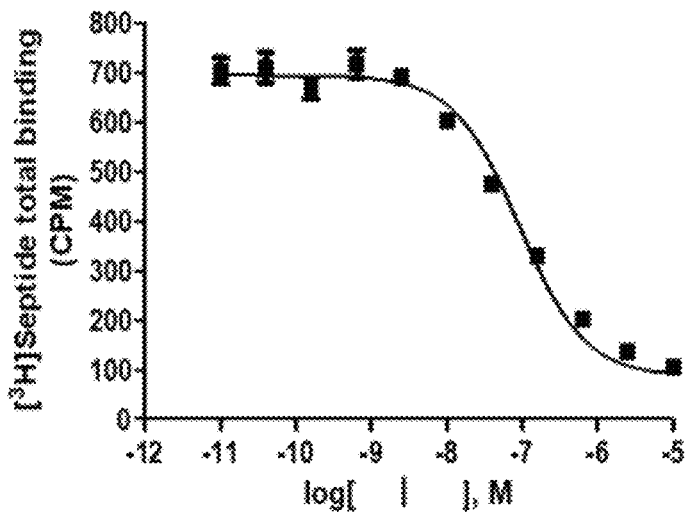
FIG. 2I is a graph of a human NK1 Receptor (hNK1R) displacement curve for heptapeptide analog I (SEQ ID NO: 9) according to one or more embodiments of the invention.
Figure 2J:
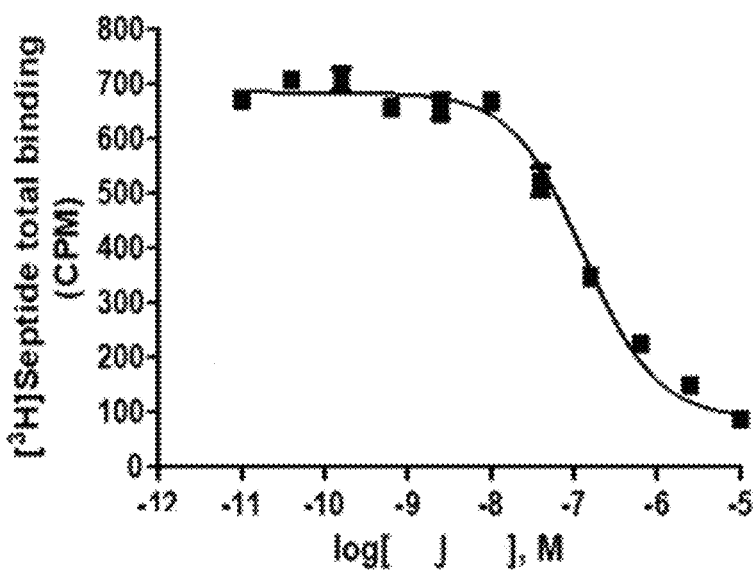
FIG. 2J is a graph of a human NK1 Receptor (hNK1R) displacement curve for heptapeptide analog J (SEQ ID NO: 10) according to one or more embodiments of the invention.
Figure 2K:
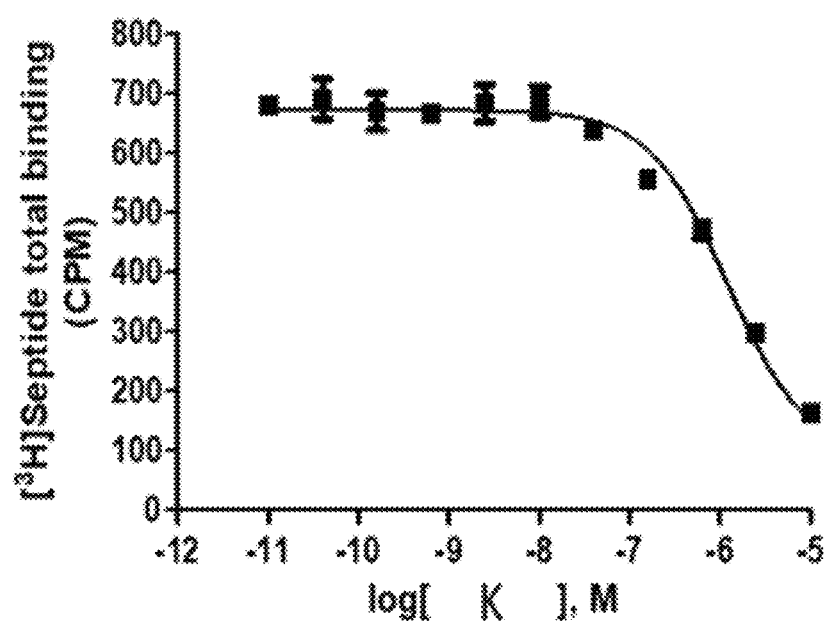
FIG. 2K is a graph of a human NK1 Receptor (hNK1R) displacement curve for heptapeptide analog K (SEQ ID NO: 11) according to one or more embodiments of the invention.
Figure 3A:
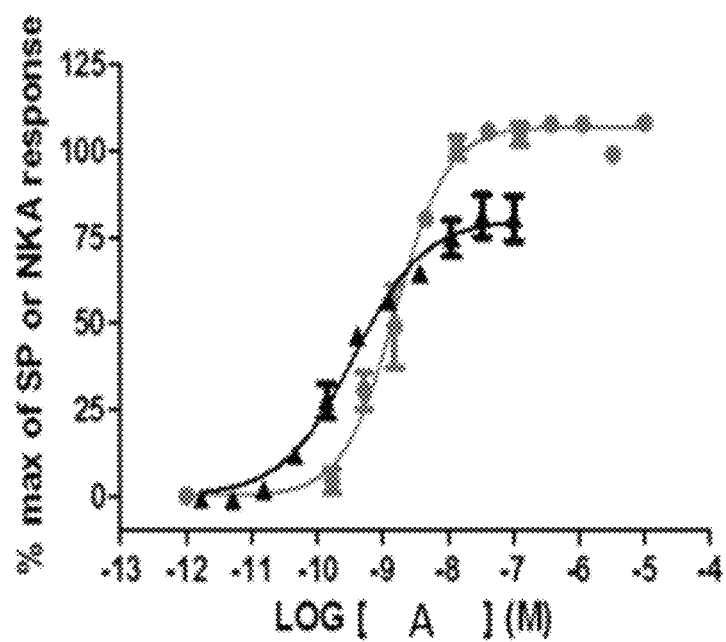
FIG. 3A is a graph showing stimulation of $[Ca^{++}]$ response by heptapeptide analog A (SEQ ID NO: 1) in Chinese hamster ovary cells (CHO cells) expressing human NK2 receptors (▼) and CHO cells expressing human NK1 receptors (●) according to one or more embodiments of the invention.
Figure 3B:
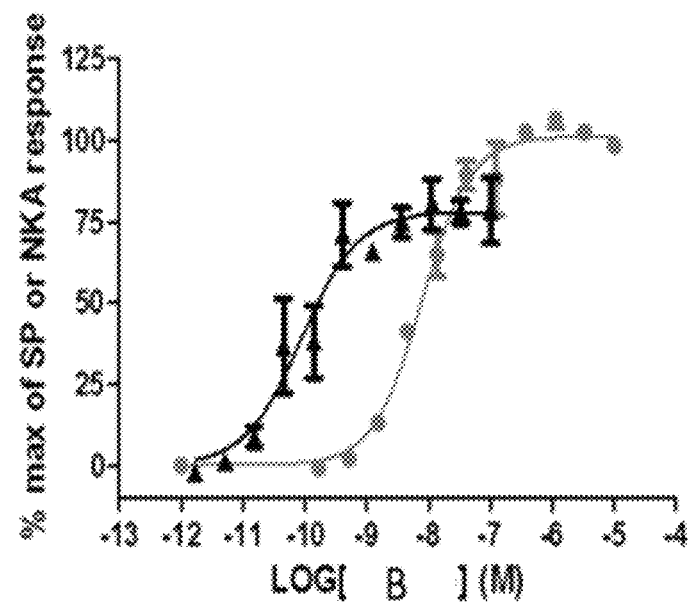
FIG. 3B is a graph showing stimulation of $[Ca^{++}]$ response by heptapeptide analog B (SEQ ID NO: 2) in Chinese hamster ovary cells (CHO cells) expressing human NK2 receptors (▼) and CHO cells expressing human NK1 receptors (●) according to one or more embodiments of the invention.
Figure 3C:
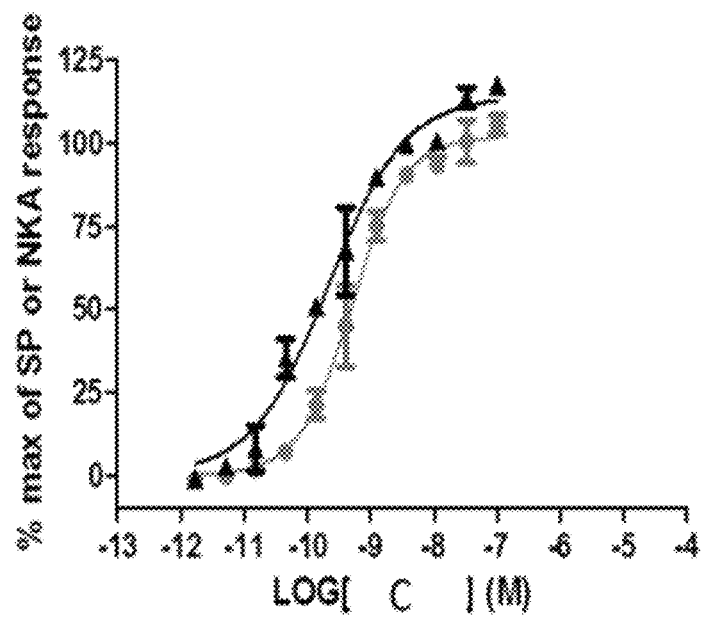
FIG. 3C is a graph showing stimulation of $[Ca^{++}]$ response by heptapeptide analog C (SEQ ID NO: 3) in Chinese hamster ovary cells (CHO cells) expressing human NK2 receptors (▼) and CHO cells expressing human NK1 receptors (●) according to one or more embodiments of the invention.
Figure 3D:
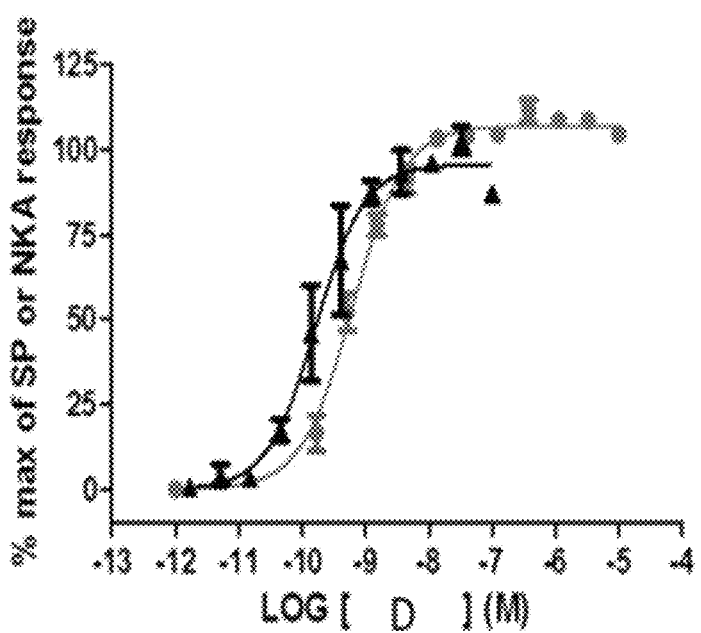
FIG. 3D is a graph showing stimulation of $[Ca^{++}]$ response by heptapeptide analog D (SEQ ID NO: 4) in Chinese hamster ovary cells (CHO cells) expressing human NK2 receptors (▼) and CHO cells expressing human NK1 receptors (●) according to one or more embodiments of the invention.
Figure 3E:
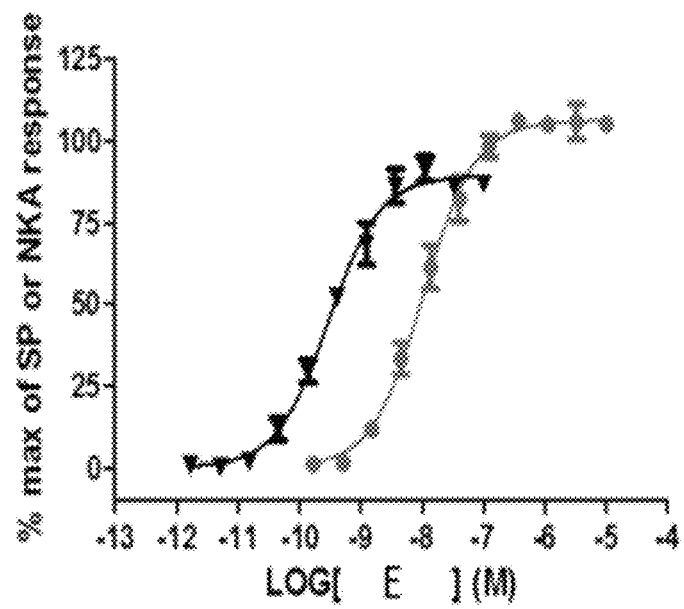
FIG. 3E is a graph showing stimulation of $[Ca^{++}]$ response by heptapeptide analog E (SEQ ID NO: 5) in Chinese hamster ovary cells (CHO cells) expressing human NK2 receptors (▼) and CHO cells expressing human NK1 receptors (●) according to one or more embodiments of the invention.
Figure 3F:
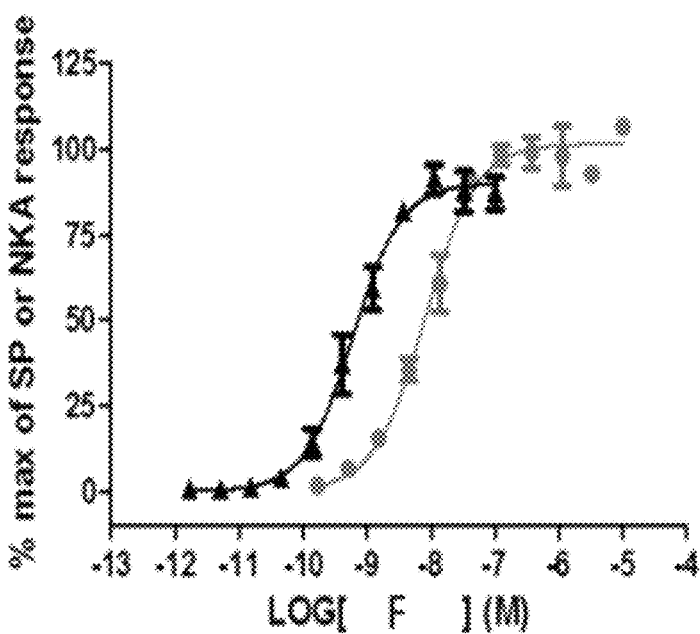
FIG. 3F is a graph showing stimulation of $[Ca^{++}]$ response by heptapeptide analog F (SEQ ID NO: 6) in Chinese hamster ovary cells (CHO cells) expressing human NK2 receptors (▼) and CHO cells expressing human NK1 receptors (●) according to one or more embodiments of the invention.
Figure 3G:
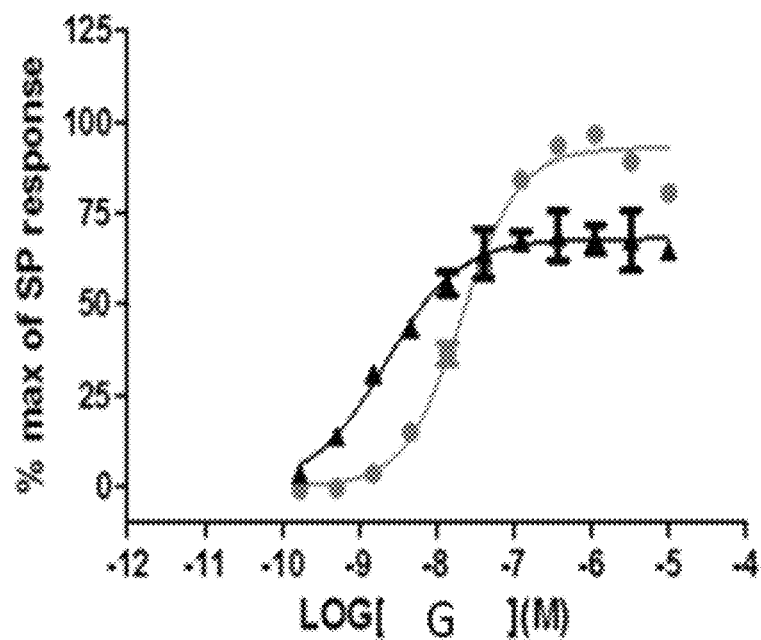
FIG. 3G is a graph showing stimulation of $[Ca^{++}]$ response by heptapeptide analog G (SEQ ID NO: 7) in Chinese hamster ovary cells (CHO cells) expressing human NK2 receptors (▼) and CHO cells expressing human NK1 receptors (●) according to one or more embodiments of the invention.
Figure 3H:
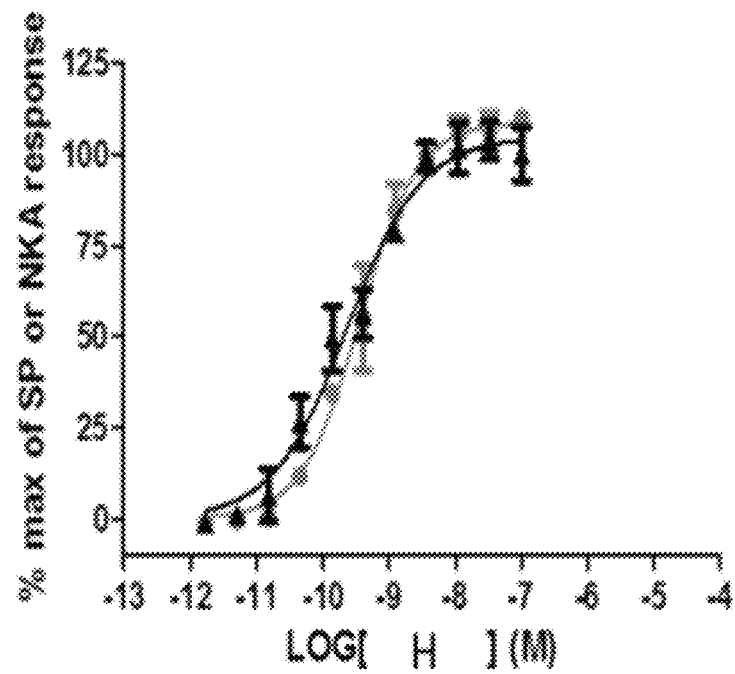
FIG. 3H is a graph showing stimulation of $[Ca^{++}]$ response by heptapeptide analog H (SEQ ID NO: 8) in Chinese hamster ovary cells (CHO cells) expressing human NK2 receptors (▼) and CHO cells expressing human NK1 receptors (●) according to one or more embodiments of the invention.
Figure 3I:
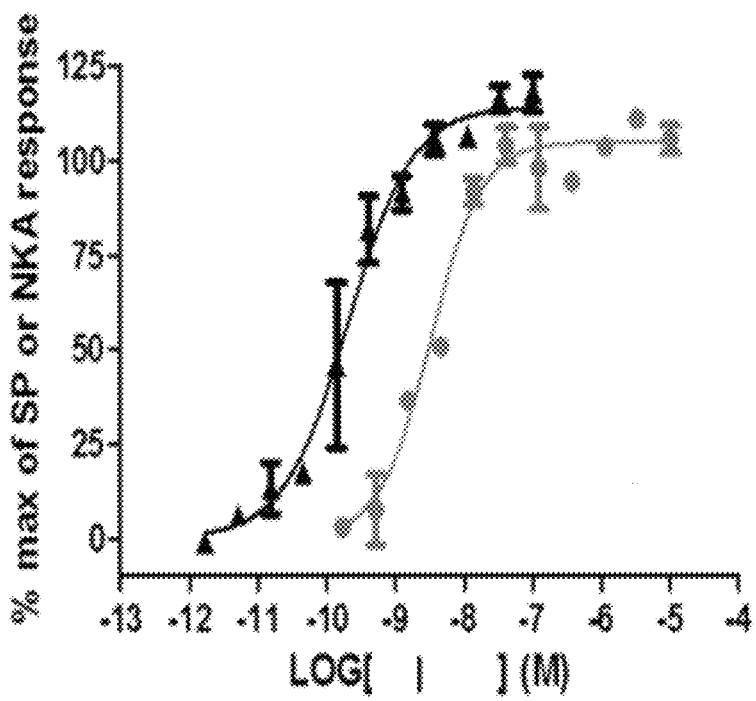
FIG. 3I is a graph showing stimulation of $[Ca^{++}]$ response by heptapeptide analog I (SEQ ID NO: 9) in Chinese hamster ovary cells (CHO cells) expressing human NK2 receptors (▼) and CHO cells expressing human NK1 receptors (●) according to one or more embodiments of the invention.
Figure 3J:
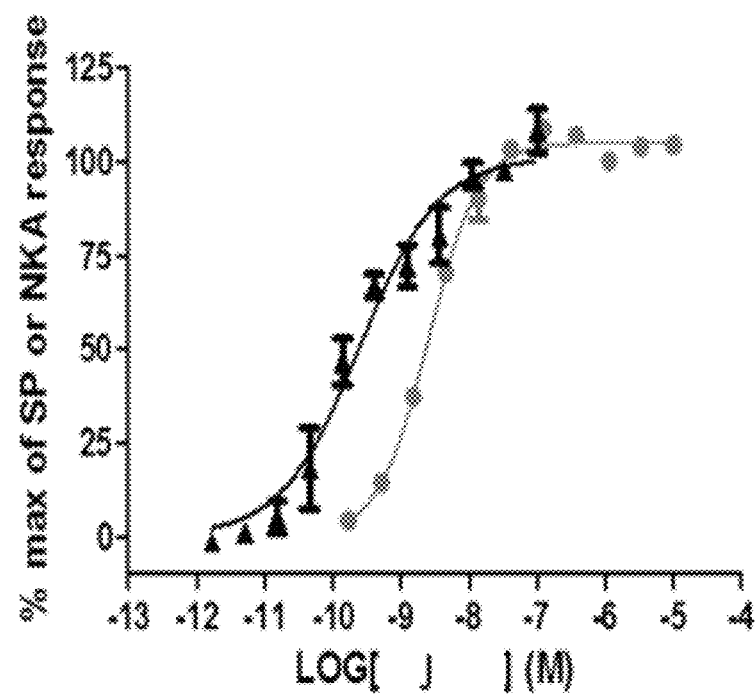
FIG. 3J is a graph showing stimulation of $[Ca^{++}]$ response by heptapeptide analog J (SEQ ID NO: 10) in Chinese hamster ovary cells (CHO cells) expressing human NK2 receptors (▼) and CHO cells expressing human NK1 receptors (●) according to one or more embodiments of the invention.
Figure 3K:
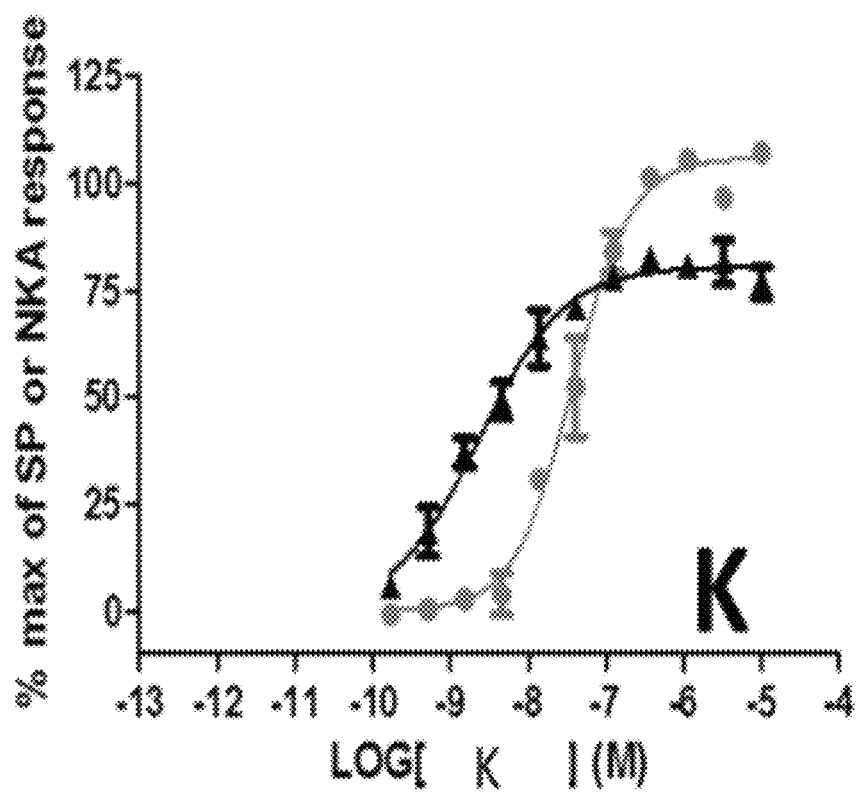
FIG. 3K is a graph showing stimulation of $[Ca^{++}]$ response by heptapeptide analog K (SEQ ID NO: 11) in Chinese hamster ovary cells (CHO cells) expressing human NK2 receptors (▼) and CHO cells expressing human NK1 receptors (●) according to one or more embodiments of the invention.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range. In addition, as used herein, the term "about", when referring to a value or to an amount of distance, diameter, mass, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed compositions and methods. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

By an "effective" amount or a "therapeutically effective amount" of a drug or pharmacologically active agent of the present disclosure including, for example, a peptide including (SEQ ID NOs: 1-11), or a pharmaceutically acceptable salt thereof, is meant a nontoxic but sufficient amount of the drug or active agent to provide the desired effect, i.e., treating urinary voiding and/or defecation dysfunction such as effectuating voluntary urinary voiding and/or defecation and/or relieving urinary and/or fecal incontinence. It is recognized that the effective amount of a drug or pharmacologically active agent will vary depending on the route of administration, the selected peptide, and the species to which the drug or pharmacologically active agent is administered. It is also recognized that one of skill in the art will determine appropriate effective amounts by taking into account such factors as metabolism, bioavailability, and other factors that affect levels of a drug or pharmacologically active agent following administration within the unit dose ranges disclosed further herein for different routes of administration.

By "pharmaceutically acceptable," such as in the recitation of a "pharmaceutically acceptable excipient," or a "pharmaceutically acceptable salt," is meant a material that is not biologically or otherwise undesirable, i.e., the material may be incorporated into a pharmaceutical composition administered to a patient or subject without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound. When the term "pharmaceutically acceptable" is used to refer to a derivative (e.g., a salt) of an active agent, it is to be understood that the derivative is pharmacologically active as well, i.e., therapeutically effective for treating urinary voiding and/or defecation dysfunction.

By "as-needed" dosing, also known as "pro re nata" or "prn" dosing, and "on demand" dosing or administration is meant the administration of a single dose of the active agent at some time prior to commencement of emptying of the bladder or bowel. Administration can be immediately prior to such a time, including about 1 minute, about 1 to about 5 minutes, about 1 to about 10 minutes, about 1 to about 20 minutes, about 1 to about 30 minutes, or about 1 to about 40 minutes, prior to such a time, depending on the formulation and the route of administration.

By "rapid-onset" is intended any period of time up to and including between about 1 sec to about 1 hour, between about 1 sec to about 45 minutes, between about 1 sec to about 30 minutes, between about 1 sec to about 15 minutes, or between about 1 sec to about 10 minutes, or between 1 sec to 5 min, after active agent administration.

By "short duration of action" is intended a duration between about 2 hours to about 10 minutes, between about 1 hour to about 10 minutes, and between about 30 minutes to about 10 minutes, and between 15 to about 5 minutes after active agent administration.

The term "immediate release" is used in its conventional sense to refer to a drug formulation that provides for release of the drug immediately after drug administration.

By the term "transdermal" drug delivery is meant delivery by passage of a drug through the skin or mucosal tissue and into the bloodstream.

The term "topical administration" is used in its conventional sense to mean delivery of a topical drug or pharmacologically active agent to the skin or mucosa.

The term "inhalation administration" is used in its conventional sense to mean delivery of an aerosolized form of the drug by passage through the nose or mouth during inhalation and passage of the drug through the walls of the lungs.

By the term "parenteral" drug delivery is meant delivery by passage of a drug into the blood stream without first having to pass through the alimentary canal, or digestive tract. Parenteral drug delivery may be "subcutaneous," referring to delivery of a drug by administration under the skin. Another form of parenteral drug delivery is "intramuscular," referring to delivery of a drug by administration into muscle tissue. Another form of parenteral drug delivery is "intradermal," referring to delivery of a drug by administration into the skin. An additional form of parenteral drug delivery is "intravenous" or "i.v." or "IV" referring to delivery of a drug by administration into a vein. An additional form of parenteral drug delivery is "intra-arterial," referring to delivery of a drug by administration into an artery. Another form of parenteral drug delivery is "transdermal," referring to delivery of a drug by passage of the drug through the skin and into the bloodstream.

Still another form of parenteral drug delivery is "transmucosal," referring to administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "lingual" drug delivery, which refers to delivery of a drug by passage of a drug through an individual's lingual mucosa and into the bloodstream. Another form of transmucosal drug delivery herein is "sublingual" drug delivery, which refers to delivery of a drug by passage of a drug through an individual's sublingual mucosa and into the bloodstream. Another form of transmucosal drug delivery is "nasal" or "intranasal" drug delivery, referring to delivery of a drug through an individual's nasal mucosa and into the bloodstream. An additional form of transmucosal drug delivery herein is "rectal" or "transrectal" drug delivery, referring to delivery of a drug by passage of a drug through an individual's rectal mucosa and into the bloodstream.

Eleven synthetic peptide analogs of the endogenous peptide, neurokinin A (NKA), are provided as therapeutics to stimulate bladder and rectal voiding in patients on an as-needed basis. The peptide analogs of the present disclosure are agonists acting at tachykinin NK2 receptors (NK2R). NK2Rs are expressed on smooth muscle in urinary, gastrointestinal, and respiratory tissues. The endogenous peptide NKA has been shown to contract bladder and colon smooth muscle preparations from various species (including human) (see for example, Mussap et al, 1996; Parlani et al, 1996; Warner et al, 2002, 2003; Burcher et al, 2008; Carini et al, 2001; Mule et al, 2000). However, the ability to contract bladder and GI smooth muscle is not sufficient to suggest clinical utility of a NK2R agonist for drug-induced voiding because coordinated, synergistic relaxation of the urethral and anal sphincters must accompany the bladder and colon contractions. For example, Palea et al (1996) found that an NK2R agonist did indeed induce contraction of human prostatic urethral smooth muscle, suggesting that occlusion of the urethra might occur simultaneously with contraction of the bladder. Simultaneous, dyssynergic contraction of both urethral and bladder smooth muscle would be highly undesirable, resulting in secondary obstructive voiding and an elevation in bladder pressure that might cause renal damage.

The 11 peptide analogs (SEQ ID NOs: 1-11; see Table 1 below and EXAMPLE 1) are provided herein for use as pharmaceutical compositions to facilitate on-demand micturition and defecation to improve the quality of patient lives and address this unmet medical need. The 11 peptide analogs (SEQ ID NOs: 1-11) may also be referred to as Compounds A-K (see Table 1 below) and the terms "peptide analog", "peptide", "compound", and "active agent" are herein used interchangeably for the purposes of the specification and claims.

TABLE 1

Heptapeptides A-K (SEQ ID NOS: 1-11) synthesized according to standard Fmoc-mediated solid-phase techniques and purified by C18 reverse-phase HPLC.

| SEQ ID NO: | Cmpd | Sequence | HPLC Purity | [M + H]+ | Saline Solubility (mg/mL) |
|---|---|---|---|---|---|
| 1 | A | Asp-Lys-Phe-Val-Gly-(NMe-Leu)-Met-NH2 | 98 | 820 | ≥20 |
| 2 | B | Asp-Arg-Phe-Val-Gly-(NMe-Leu)-Nle-NH2 | 99 | 832 | ≥20 |
| 3 | C | Asp-Arg-Phe-Val-Gly-(NMe-Leu)-Met-NH2 | 98 | 850 | ≥20 |
| 4 | D | Asp-Lys-Phe-Val-Gly-Leu-Met-NH2 | 95 | 808 | <1 |
| 5 | E | Asp-Lys-Phe-Val-(β-Ala)-Leu-Met-NH2 | 96 | 822 | <1 |
| 6 | F | Asp-Lys-Phe-Val-Gly-Leu-Nle-NH2 | 95 | 790 | <1 |
| 7 | G | Asp-Lys-Phe-Val-(β-Ala)-Leu-Nle-NH2 | 99 | 804 | <1 |
| 8 | H | Asp-Arg-Phe-Val-Gly-Leu-Met-NH2 | 96 | 836 | <1 |
| 9 | I | Asp-Arg-Phe-Val-(β-Ala)-Leu-Met-NH2 | 99 | 850 | <1 |
| 10 | J | Asp-Arg-Phe-Val-Gly-Leu-Nle-NH2 | 99 | 818 | <1 |
| 11 | K | Asp-Arg-Phe-Val-(β-Ala)-Leu-Nle-NH2 | 97 | 832 | <1 |

In one embodiment, methods are provided herein for using the peptide analogs selected from the group consisting of SEQ ID NOs: 1-11, or a pharmaceutically acceptable salt thereof, to provide "on-demand, rapid-onset, short-duration, drug-induced voiding". The peptide-induced voiding can be useful for those with voiding dysfunction or for a mammal for which inducing voiding is otherwise desirable. The compositions and methods of the present disclosure provide pharmaceutical formulations and methods of administration of smooth muscle prokinetic peptides to provide a duration of prokinetic action which can produce voiding and then allow the bladder and rectum to subsequently relax to allow for storage of newly-formed urine and stool to prevent subsequent incontinence. The formulations and methods of administration of the present disclosure can minimize the duration of side-effects in other organs systems. The prokinetic peptide formulations and methods of administration of the present disclosure can be administered multiple times per day to initiate voiding.

One advantage of the presently described subject matter is provision of smooth muscle prokinetic agents, peptides SEQ ID NOs: 1-11, that have a rapid-onset and short duration of action for administration to mammals to achieve a rapid-onset and short duration contraction of the rectum and bladder. In one embodiment, the majority of the effects of the peptide are terminated within about 20 minutes. In one embodiment, the majority of the effects of the peptide are terminated within about 10 minutes. In one embodiment, the majority of the effects of the peptide are terminated within about 5 minutes.

Another advantage of the presently described subject matter is that the peptide-induced voiding can be achieved without intolerable contractions of the stomach and bowel to produce vomiting and painful cramps.

Another advantage of the presently described subject matter is that the peptide-induced voiding can be achieved without the adverse effect of contraction of respiratory smooth muscles and difficulty breathing. This is an unexpected advantage, given the presence of NK2 receptors in the respiratory tract, where NK2 receptor stimulation can be expected to cause contraction of the tracheal and bronchial smooth muscle to close the airways.

One advantage of the peptides provided herein for as-needed or "on demand" voiding is that they are rapidly inactivated in vivo. Voiding can thus be completed within around 5 to 20 minutes or within around 5 to 10β minutes of administration, without residual contractile activity until the next on-demand administration.

Notwithstanding the attraction of the approach of using compounds with a rapid onset of action and a short duration of action, it is not without complications. A significant liability of peptide NK2 agonists is their limited selectivity to activate NK2 over NK1 receptors. For example, despite its weak ability to displace radiolabeled substance P from recombinant NK1 receptors, NKA is a potent NK1 receptor agonist in functional assays and binds with subnanomolar affinity to a "septide-sensitive" site on NK1 receptors (Sagan et al, 1996; Hastrup & Schwartz, 1996; Torrens et al, 2000). Activation of NK1 receptors most likely explains the skin flushing observed after infusion of NKA in human studies since dermal vasodilation is a well recognized response to intra-arterial infusion of substance P (Newby et al, 1997). The ability of NKA to activate NK1 receptors via the septide site may confer adverse effects and limit margins of safety because NK1 receptors have a widespread distribution throughout the body and are involved in many physiological systems, including cardiovascular, respiratory, inflammatory, and immune responses. Examples of physiological systems that can be activated by NKA via NK1 receptors include NKA-induced hypotension in rats that can be abolished after blockade of NK1 (but not NK2) receptors (Kaczynska et al, 2016), and bronchoconstriction induced by NKA in guinea-pigs that had an NK1 receptor mediated component (Ricciardolo et al, 2000). There is also a potential for widespread organ toxicity on chronic exposure to compounds that activate NK1 receptors since such activation has been implicated in hepatic injury caused by toxins (Bang et al, 2003; Yang et al, 2013), and kidney damage caused by hypertension (Wang and Wang, 2012). Therefore, NK2 agonists with selectivity for activation of NK2 receptors over septide-sensitive sites on NK1 receptors can be useful to minimize NK1 receptor-mediated adverse effects and toxicity. The selectivity for NK2 receptors over NK1 receptors is provided for the eleven NKA analogs disclosed herein.

In one embodiment, the presently disclosed subject matter provides a functional assay for NK1 receptor activation in the target organ of toxicity. Given that in the cardiovascular system vascular tone and blood pressure may be altered by activation of NK1 receptors located in the brainstem, vagal sensory nerves, and/or vascular endothelial cells (Feldman, 1995; Bowden et al, 1996; Jafri and Weinreich, 1996; Miike et al, 2009) it is unclear which physiological system or target tissue would best predict undesirable NK1 agonist mediated effects in humans. Specifically, which of these is the primary site responsible for NK1 agonist mediated hypotension in vivo is not clear. Moreover, even when examining a single tissue, differences in the receptor reserve of G-protein coupled receptors exist between species (and in different tissues within a species) that alter the efficacy of agonists (Oriowo et al, 1989; Drury et al, 1998). These complications, along with the potential for crosstalk with other receptors expressed in native tissues, made it unfeasible to develop a functional assay to reliably predict the potential for NK1-mediated toxicity of NK2 agonists in humans. Instead, intracellular calcium mobilization was employed as a functional assay of relative agonist efficacy and potency using human recombinant NK2 and NK1 receptors expressed in CHO cells. These single receptor systems permit examination of effects of compounds on NK2 and NK1 receptors independently of each other. The binding to, and activation of, human NK2 Receptor (hNK2R) and human NK1 Receptor (hNK1R) by the eleven peptide analogs (SEQ ID NOs: 1-11) are described in EXAMPLES 2 and 3 herein below.

EXAMPLE 2 describes radioligand competition binding assays to determine the receptor affinities and selectivity of compounds A-K (SEQ ID NOs: 1-11) for hNK2R and hNK1R. Displacement curves for [125I]-NKA binding to hNK2Rs for the 11 heptapeptide analogs of NKA are shown in FIGS. 1A-1K. Most Hill slopes approached unity, ranging from −0.8 to −0.9. All test compounds competed for [125I]-NKA binding to hNK2Rs, with Compounds C (SEQ ID NO: 3) and A (SEQ ID NO: 1) demonstrating the highest affinity, and Compounds K (SEQ ID NO: 11) and G (SEQ ID NO: 7) demonstrating the lowest affinity for hNK2Rs (see Table 2 below). Displacement curves for displacement of [3H] septide binding to hNK1Rs for the 11 heptapeptide analogs of NKA are shown in FIGS. 2A-2K. Most Hill slopes approached unity, ranging from −0.8 to 1.1. All compounds competed for [3H] septide binding to hNK1Rs, with Compounds H (SEQ ID NO: 8) and D (SEQ ID NO: 4) demonstrating the highest affinity, and Compounds K (SEQ ID NO: 11) and G (SEQ ID NO: 7) demonstrating the lowest affinity for hNK1Rs (Table 2). The ratios of Kis for hNK1R/hNK2R reveal the selectivity for binding to hNK1Rs vs hNK2Rs. Table 2 shows that Compounds B (SEQ ID NO: 2), A (SEQ ID NO: 1), G (SEQ ID NO: 7), K (SEQ ID NO: 11), and C (SEQ ID NO: 3) exhibit the greatest selectivity as they were all >150-fold more selective for hNK2Rs in this assay.

and G (SEQ ID NO: 7) the least potent (see Table 3) at the hNK2R. All the compounds elicited concentration-dependent calcium responses (FIGS. 3A-3K) and were full agonists at the human NK1R (>90% maximal response compared to Substance P). Compounds H (SEQ ID NO: 8) and

TABLE 2

Summary of binding affinities for human NK2Rs and NK1Rs.

| SEQ ID NO: | Compound | Sequence | hNK2 binding Ki (nM) | hNK1 binding Ki (nM) | hNK2 selectivity ratio |
|---|---|---|---|---|---|
| 1 | A | Asp-Lys-Phe-Val-Gly-(NMe-Leu)-Met-NH2 | 0.20 | 50.12 | 248.89 |
| 2 | B | Asp-Arg-Phe-Val-Gly-(NMe-Leu)-Nle-NH2 | 0.59 | 331.13 | 557.83 |
| 3 | C | Asp-Arg-Phe-Val-Gly-(NMe-Leu)-Met-NH2 | 0.12 | 20.89 | 167.49 |
| 4 | D | Asp-Lys-Phe-Val-Gly-Leu-Met-NH2 | 0.38 | 15.85 | 41.64 |
| 5 | E | Asp-Lys-Phe-Val-(β-Ala)-Leu-Met-NH2 | 2.11 | 257.04 | 122.04 |
| 6 | F | Asp-Lys-Phe-Val-Gly-Leu-Nle-NH2 | 2.75 | 223.87 | 81.47 |
| 7 | G | Asp-Lys-Phe-Val-(β-Ala)-Leu-Nle-NH2 | 16.39 | 3090.30 | 188.58 |
| 8 | H | Asp-Arg-Phe-Val-Gly-Leu-Met-NH2 | 0.31 | 8.32 | 27.10 |
| 9 | I | Asp-Arg-Phe-Val-(β-Ala)-Leu-Met-NH2 | 0.88 | 95.50 | 108.27 |
| 10 | J | Asp-Arg-Phe-Val-Gly-Leu-Nle-NH2 | 1.74 | 125.89 | 72.53 |
| 11 | K | Asp-Arg-Phe-Val-(β-Ala)-Leu-Nle-NH2 | 6.85 | 1202.26 | 175.59 |

EXAMPLE 3 describes intracellular calcium mobilization by in vitro activation of recombinant hNK1Rs or hNK2Rs expressed in CHO cells by the 11 heptapeptide analogs. All the compounds elicited concentration-dependent calcium responses (FIGS. 3A-3K) and were full agonists at the hNK2R (>80% maximal response compared to Neurokinin A). Compounds B (SEQ ID NO: 2) and D (SEQ ID NO: 4) were the most potent and Compounds K (SEQ ID NO: 11) C (SEQ ID NO: 3) were the most potent and Compounds K (SEQ ID NO: 11) and G (SEQ ID NO: 7) the least potent (see Table 3) at the hNK1R. The ratios of EC50s for hNKR1/hNK2R reveal the selectivity for activation of hNK1Rs vs hNK2Rs. Table 3 shows that Compounds K (SEQ ID NO: 11), G (SEQ ID NO: 7), E (SEQ ID NO: 5) and B (SEQ ID NO: 2) exhibit the greatest selectivity as they were all >20-fold more selective for hNK2Rs in this assay.

TABLE 3

Summary of in vitro functional potency at human NK2Rs and NK1Rs.

| SEQ ID NO: | Compound | Sequence | hNK2 EC50 (nM) | hNK1 EC50 (nM) | hNK2 selectivity ratio |
|---|---|---|---|---|---|
| 1 | A | Asp-Lys-Phe-Val-Gly-(NMe-Leu)-Met-NH2 | 0.14 | 0.95 | 7 |
| 2 | B | Asp-Arg-Phe-Val-Gly-(NMe-Leu)-Nle-NH2 | 0.08 | 5.84 | 70 |
| 3 | C | Asp-Arg-Phe-Val-Gly-(NMe-Leu)-Met-NH2 | 0.16 | 0.3 | 2 |
| 4 | D | Asp-Lys-Phe-Val-Gly-Leu-Met-NH2 | 0.09 | 0.41 | 5 |
| 5 | E | Asp-Lys-Phe-Val-(β-Ala)-Leu-Met-NH2 | 0.18 | 6.31 | 36 |
| 6 | F | Asp-Lys-Phe-Val-Gly-Leu-Nle-NH2 | 0.38 | 2.36 | 6 |
| 7 | G | Asp-Lys-Phe-Val-(β-Ala)-Leu-Nle-NH2 | 3 | 78.22 | 26 |
| 8 | H | Asp-Arg-Phe-Val-Gly-Leu-Met-NH2 | 0.19 | 0.16 | 0.8 |
| 9 | I | Asp-Arg-Phe-Val-(β-Ala)-Leu-Met-NH2 | 0.15 | 1.83 | 12 |
| 10 | J | Asp-Arg-Phe-Val-Gly-Leu-Nle-NH2 | 0.2 | 1.71 | 9 |
| 11 | K | Asp-Arg-Phe-Val-(β-Ala)-Leu-Nle-NH2 | 1.16 | 29.51 | 25 |

EXAMPLE 4 describes determination of the pharmacokinetic (PK) profiles of selected compounds by measurement in rat plasma after intravenous (IV) bolus dosing. Plasma concentrations of soluble compounds A (SEQ ID NO: 1) and B (SEQ ID NO: 2) decreased rapidly ($t_{1/2}$=0.2-1.2 min) to levels <1 ng/mL by 10 min post-dose (see FIG. 4A). In addition, plasma concentrations of insoluble compounds K (SEQ ID NO: 11), G (SEQ ID NO: 7), and E (SEQ ID NO: 5) also decreased rapidly ($t_{1/2}$=3.3-4.7 min) (see FIG. 4B). Thus, these compounds can demonstrate rapid pharmacokinetics with fast plasma half-lives of <5 min.

Figure 5:
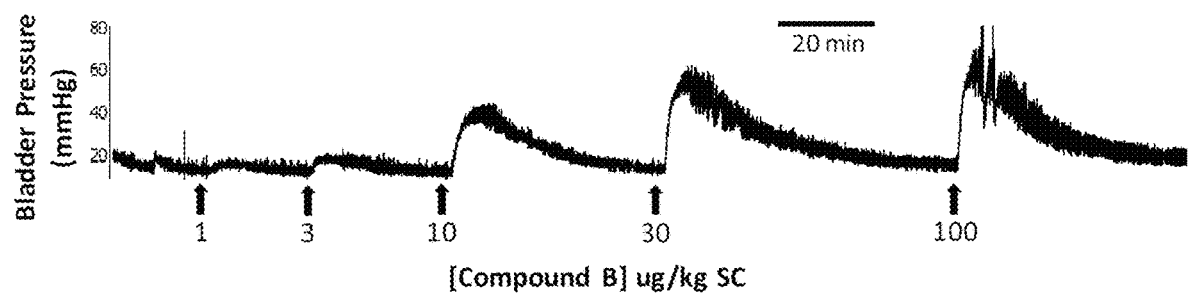
FIG. 5 is a physiograph tracing showing the rapid dose-related increase in bladder pressure after consecutive injections of heptapeptide analog B (SEQ ID NO: 2) (1-100 µg/kg subcutaneous (SC), indicated by each arrow) in an anesthetized acute spinal cord injured (aSCI) rat according to one or more embodiments of the invention.
Figure 6A:
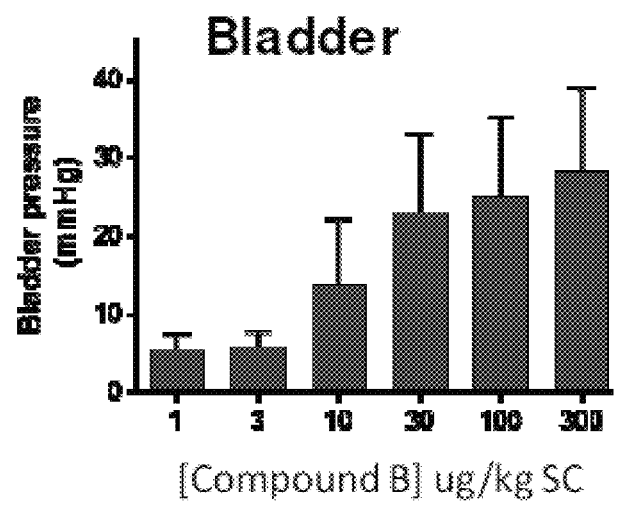
FIG. 6A is a graph showing a dose-related increase in bladder pressure after consecutive subcutaneous (SC) administrations of heptapeptide analog B (SEQ ID NO: 2) in anesthetized acute spinal cord injured (aSCI) rats according to one or more embodiments of the invention. Data are mean+SD of peak bladder pressure during the first 5 min after each dose. N=4-6 for all doses.
Figure 6B:
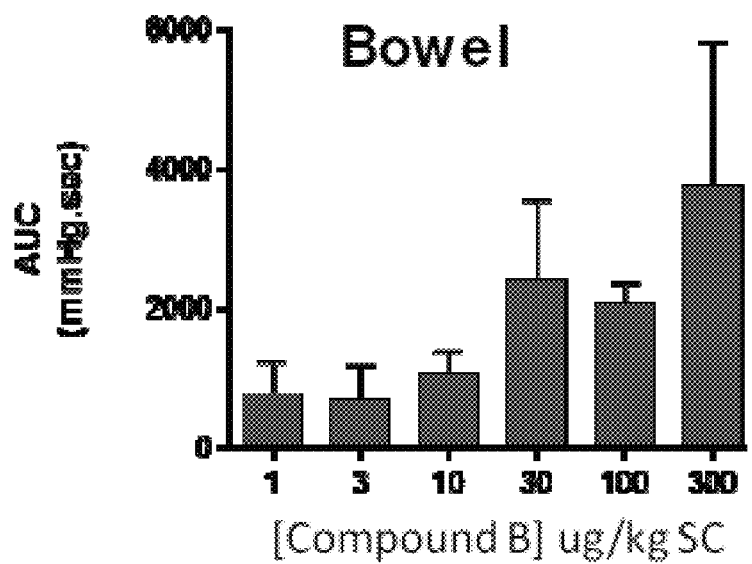
FIG. 6B is a graph showing dose-related increase in bowel activity after consecutive SC administrations of heptapeptide analog B (SEQ ID NO: 2) in an anesthetized acute spinal cord injured (aSCI) rat according to one or more embodiments of the invention. Data are mean+SD of bowel pressure area under the curve (AUC) for the first 5 min after each dose. N=4-6 for all doses.

EXAMPLE 5 describes compound B (SEQ ID NO: 2) administration to rats to evaluate effects on bladder and bowel activity and to demonstrate efficacy following subcutaneous (SC) dosing. FIG. 5 is a physiograph tracing showing a rapid dose-related increase in bladder pressure after consecutive injections of Compound B (SEQ ID NO: 2) (1-100 µg/kg SC, indicated by each arrow) in an anesthetized aSCI rat. The duration of action at the maximal dose tested was 15 to 30 min SC administration of Compound B (SEQ ID NO: 2) evoked a dose related, fast onset (<2 min) increase in bladder contraction pressure (see FIG. 5). FIGS. 6A and 6B show dose related increases in bladder (6A) and bowel (6B) activity after consecutive SC administrations of Compound B (SEQ ID NO: 2) in the acute SCI rat. At doses >10 µg/kg SC, Compound B (SEQ ID NO: 2) produced measurable increases in bladder activity (see FIG. 6A). At doses >10 µg/kg SC, Compound B (SEQ ID NO: 2) produced measurable increases in bowel activity (see FIG. 6B). Compound B (SEQ ID NO: 2) induced a fast onset, short duration bladder contraction, and dose-related increases in both bladder and bowel pressure following SC dose administration.

Figure 7:
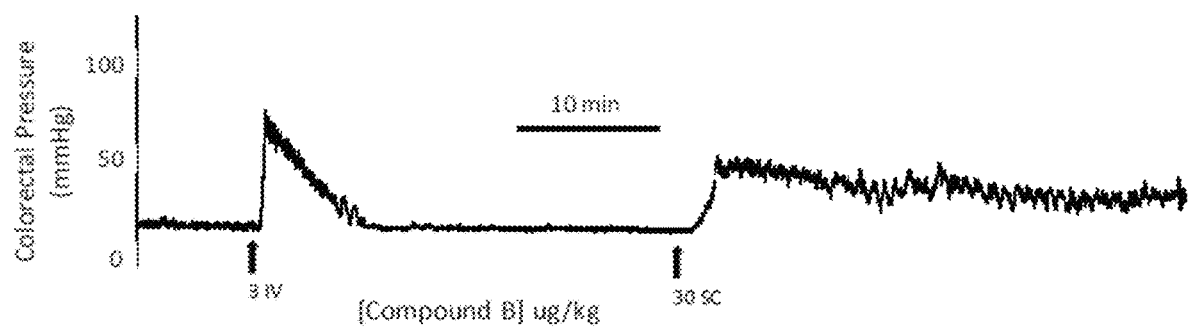
FIG. 7 is a physiograph trace of colorectal pressure recorded from an anesthetized dog after heptapeptide analog B (SEQ ID NO: 2) was dissolved in saline and administered as an intravenous (IV) bolus injection (3 μg/kg) or subcutaneous (SC) injection (30 μg/kg) according to one or more embodiments of the invention.
Figure 8:
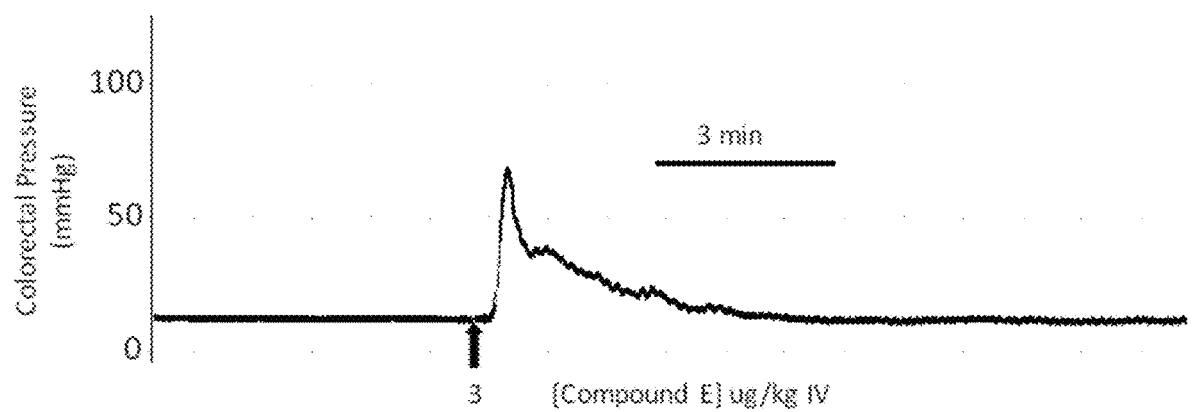
FIG. 8 is a physiograph trace of colorectal pressure recorded from an anesthetized dog after heptapeptide analog E (SEQ ID NO: 5) was dissolved in 50% DMSO in saline and administered as an intravenous (IV) bolus injection (3 μg/kg) according to one or more embodiments of the invention.
Figure 9:
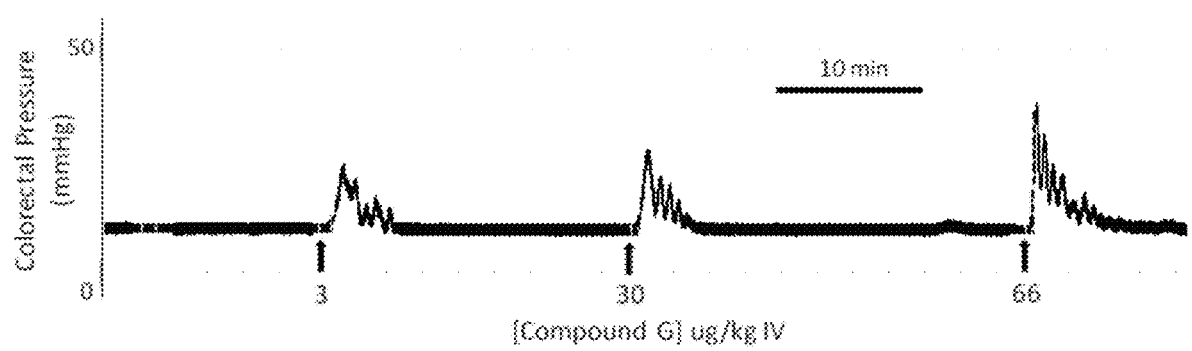
FIG. 9 is a physiograph trace of colorectal pressure recorded from an anesthetized dog after heptapeptide analog G (SEQ ID NO: 7) was dissolved in 50% DMSO in saline and administered as consecutive intravenous (IV) bolus injections (3, 30 and 66 ug/kg), which the trace illustrates each produced dose-related, rapid (within 1 minute) increases in colorectal pressure lasting approximately 5 minutes according to one or more embodiments of the invention.

EXAMPLE 6 describes administration of compounds B (SEQ ID NO: 2), E (SEQ ID NO: 5) and G (SEQ ID NO: 7) to dogs to evaluate effects on bladder and bowel activity and to demonstrate efficacy following IV and SC dosing. FIG. 7 shows a physiograph trace of colorectal pressure recorded from an anesthetized dog. Both IV and SC doses of Compound B (SEQ ID NO: 2) produced a rapid (within 3 minutes) increase in colorectal pressure. The response to IV lasted approximately 7 minutes and the SC dose lasted over 30 minutes. Both doses produced leakage of urine from the bladder consistent with increase bladder pressures and induction of voiding (data not shown). FIG. 8 shows a physiograph trace of colorectal pressure recorded from an anesthetized dog after IV bolus injection (3 µg/kg) of compound E (SEQ ID NO: 5) producing a rapid (within 1 minute) increase in colorectal pressure lasting approximately 4 minutes. FIG. 9 shows a physiograph trace of colorectal pressure recorded from an anesthetized dog after administration of IV bolus injections (3, 30 and 66 ug/kg) of Compound G (SEQ ID NO: 7), producing dose-dependent, rapid (within 1 minute) increases in colorectal pressure all lasting approximately 5 minutes.

In one embodiment of the presently disclosed subject matter, a synthetic peptide is provided selected from the group consisting of an amino acid sequence: Asp-Lys-Phe-Val-Gly-(NMe-Leu)-Met-NH2 (SEQ ID NO: 1), Asp-Arg-Phe-Val-Gly-(NMe-Leu)-Nle-NH2 (SEQ ID NO: 2), Asp-Arg-Phe-Val-Gly-(NMe-Leu)-Met-NH2 (SEQ ID NO: 3), Asp-Lys-Phe-Val-Gly-Leu-Met-NH2 (SEQ ID NO: 4), Asp-Lys-Phe-Val-(β-Ala)-Leu-Met-NH2 (SEQ ID NO: 5), Asp-Lys-Phe-Val-Gly-Leu-Nle-NH2 (SEQ ID NO: 6), Asp-Lys-Phe-Val-(β-Ala)-Leu-Nle-NH2 (SEQ ID NO: 7), Asp-Arg-Phe-Val-Gly-Leu-Met-NH2 (SEQ ID NO: 8), Asp-Arg-Phe-Val-(β-Ala)-Leu-Met-NH2 (SEQ ID NO: 9), Asp-Arg-Phe-Val-Gly-Leu-Nle-NH2 (SEQ ID NO: 10), and Asp-Arg-Phe-Val-(β-Ala)-Leu-Nle-NH2 (SEQ ID NO: 11).

In one embodiment, a method is provided for preparing a peptide selected from the group consisting of SEQ ID NOs: 1-11. The method includes chemically synthesizing a peptide consisting essentially of, or consisting of, an amino acid sequence of any one of SEQ ID NOs: 1-11; and purifying the peptide. The chemical synthesis step can include solid phase chemical synthesis. The purification step can include reverse phase chromatography.

In one embodiment, a pharmaceutical composition is provided that includes as the active agent a peptide selected from SEQ ID NOs: 1-11, or a pharmaceutically acceptable salt thereof. The pharmaceutical composition can be useful for inducing as-needed or "on demand" urinary voiding and/or defecation in a mammal. The pharmaceutical composition may further include a pharmaceutically acceptable excipient.

In one embodiment, pharmaceutical compositions are provided having as the active agent a peptide selected from SEQ ID NOs: 1-3, or a pharmaceutically acceptable salt thereof, in a formulation beneficial for a hydrophilic active ingredient. The peptides having SEQ ID NOs: 1-3 are hydrophilic and pharmaceutical formulations beneficial for the administration of such hydrophilic active ingredients are known and prepared according to procedures standard in the art. In one embodiment, the hydrophilic peptides of the present disclosure can be formulated and administered in aqueous isotonic solution according to procedures known in the art such as, for example, those described in Strickley (2004) Pharmaceutical Research, 21(2): 201-230). The hydrophilic peptides that are ionizable can be solubilized for dose administration by adjustment of the formulation pH to an acceptable value within a range between pH 2-12. Formulation pH can be controlled by the addition of agents such as, but not limited to, acids/bases such as hydrochloric acid or sodium hydroxide, or buffers such as glycine, citrate, acetate, histidine, phosphate, tris(hydroxymethyl)aminomethane (TRIS), or carbonate.

In one embodiment, pharmaceutical compositions are provided having as the active agent a peptide selected from SEQ ID NOs: 5, 7, and 11, or a pharmaceutically acceptable salt thereof, in a formulation beneficial for a hydrophobic active ingredient. The peptides selected from the group of SEQ ID NOs: 5, 7, and 11 are hydrophobic and pharmaceutical formulations beneficial for the administration of such hydrophobic peptide active ingredients are known and can be prepared according to procedures standard in the art. In one embodiment, the hydrophobic peptides of the present disclosure can be formulated and administered using a combination of an aqueous solution and a water soluble, bio-compatible, organic solvent/surfactant as disclosed, for example, in Strickley (Pharmaceutical Research, 21(2): 201-230, 2004). A variety of co-solvents including propylene glycol, ethanol, polyethylene glycol 300, polyethylene glycol 400, glycerin, dimethylacetamide (DMA), N-methyl-2-pyrrolidone (NMP; Pharmasolve), dimethylsulfoxide (DMSO), Solutol HS 15, Cremophor EL, Cremophor RH 60, and polysorbate 80, among others can be used as previously disclosed.

In one embodiment, parenteral formulations of the peptides of the present disclosure may include permeation enhancers such as sodium lauryl sulphate, lysophosphatidylcholine and phosphatidylcholines, polyoxyethylene 23 lauryl ether (Brij 35), quillajasaponin, alkylglycoside derivatives, sodium glycocholate, sodium cholate, sodium deoxycholate, sodium glycodeoxycholate, sodium taurocholate, chitosan and EDTA among others as disclosed, for example, by Morales and McConville (Drug Dev Ind Pharm, 40(5): 579-590, 2014).

In one embodiment, the pharmaceutical composition can further comprise a therapeutically effective amount of a NK2R antagonist, or a pharmaceutically acceptable salt thereof, wherein the onset of action of the NK2R antagonist is longer than the onset of the peptide to terminate the majority of the effects of the peptide within about 15 minutes after occurrence of the one or both of urinary voiding and defecation, wherein the NK2R antagonist has a duration of action of less than about 4 hours. The NK2R antagonist can have a duration of action of less than about 3 hours. The NK2R antagonist can have a duration of action of less than about 2 hours. The onset of action of the NK2R antagonist can be longer than the onset of the peptide to terminate the majority of the effects of the peptide within about 10 minutes after occurrence of the one or both of urinary voiding and defecation. The onset of action of the NK2R antagonist can be longer than the onset of the peptide to terminate the majority of the effects of the NK2R agonist within about 5 minutes after occurrence of the one or both of urinary voiding and defecation.

In one embodiment, a pharmaceutical composition is provided, wherein the composition includes a peptide having the amino acid sequence SEQ ID NO: 1, 2, 7 or 11 having a high degree of selectivity for NK2R versus NK1R. The phrase "a high degree of selectivity for NK2R versus NK1R" means that the ratio of the binding affinity (i.e., NK1 binding Ki/NK2 binding Ki) is at least about 100 or greater, at least about 150 or greater, or at least about 170 or greater. In one example the ratio of the binding affinity (i.e., hNK1 binding Ki/hNK2 binding Ki) is at least about 170 or greater.

In one embodiment, a method is provided for inducing one or both of urinary voiding and defecation in a mammal, which includes administering on an as-needed basis to the mammal a therapeutically effective amount of a composition comprising a peptide selected from the group consisting of SEQ ID NOs: 1-11, or a pharmaceutically acceptable salt thereof, and a pharmaceutically acceptable excipient, to induce the as-needed or "on demand" one or both of urinary voiding and defecation. The mammal can be a human or a companion animal (e.g. a cat or a dog), or a farm animal (e.g. a horse, cow, pig, or sheep).

The compositions and methods of the present disclosure meet an existing need for new treatments for urinary voiding and defecation dysfunction including, for example, the inability to voluntarily micturate or defecate. Thus, the as-needed administering may be repeated multiple times per day. The as-needed administering can be performed by one or a combination of parenteral, intravenous, topical, transdermal, intramuscular, subcutaneous, transnasal, inhalation, transrectal, lingual, sublingual, transmucosal, buccal, and transbuccal administration. The urinary retention and defecation dysfunction can be a result of a wide range of injuries, conditions, diseases, or disorders, including of one or more of spinal cord injury, traumatic brain injury, multiple sclerosis, spina bifida, degenerative brain disease, Alzheimer's, Parkinson's, dementia, diabetes, advanced age, and postoperative status, and combinations thereof. The compositions and methods can be useful for inducing urinary voiding and defecation in persons who are, for example, comatose to cause the voiding before the person voids unconsciously. Another advantage of the methods and compostions of the present disclosure is for a pet owner who may want to induce voiding in their normal dog, for example, at a specific, convenient location or time.

In the method for inducing one or both urinary voiding and defecation as-needed in a mammal, the method can further include administering a therapeutically effective amount of a NK2R antagonist, or a pharmaceutically acceptable salt thereof, to terminate at least a majority of the effects of the peptide selected from SEQ ID NOs: 1-11, wherein the NK2R antagonist has a duration of action of less than about 4 hours. The NK2R antagonist can have a duration of action of less than about 3 hours. The NK2R antagonist can have a duration of action of less than about 2 hours.

In the method for inducing one of urinary voiding and defecation as-needed in a mammal that further includes administration of the NK2R antagonist, the peptide selected from SEQ ID NOs: 1-11 and the NK2R antagonist can be co-administered in either a single or a separate formulation and the onset of action of the NK2R antagonist can be longer than the onset of the peptide to terminate the majority of the effects of the peptide within about 15 minutes. The onset of action of the NK2R antagonist can be longer than the onset of the peptide to terminate the majority of the effects of the peptide within about 10 minutes. The onset of action of the NK2R antagonist can be longer than the onset of the peptide to terminate the majority of the effects of the peptide within about 5 minutes.

In one embodiment, the NK2R antagonist can be administered subsequent to administration of the peptide and after occurrence of the one or both of urinary voiding and defecation, and the onset of action of the NK2R antagonist can range from about 1 to about 15 minutes to terminate the majority of the effects of the peptide within about 10 minutes. The onset of action of the NK2R antagonist can range from about 1 to about 10 minutes to terminate the majority of the effects of the peptide within about 10 minutes. The onset of action of the NK2R antagonist can range from about 1 to about 5 minutes to terminate the majority of the effects of the peptide within about 5 minutes.

It is understood by those of skill in the art that the timing of the administration of the NK2R antagonist in relation to the administration of the peptide can vary depending on the respective onset and duration of action of each individual peptide and antagonist chosen to induce voiding and reverse unwanted effects, respectively. The important feature of the timing of the method is that the NK2R antagonist cannot be at effective plasma concentrations during the time when voiding is desired, but must be at effective concentrations during any unwanted effects of the peptide.

In one embodiment, the administering of the peptide according to the methods and formulations of the present disclosure may be combined with one or more urethral relaxants such as, but not limited to, alpha adrenergic receptor blockers, nitric oxide (NO) donors, PDE5 inhibitors, prostaglandin E receptor (EP1,2,3) agonists, and pharmacological or electrical blockade of the pudendal nerve.

Formulations of the compositions and active agents of the present disclosure are provided in as-needed dosage forms, and can include immediate release formulations to achieve as-needed administration of the active agent.

The peptide selected from SEQ ID NOs: 1-11, or the pharmaceutically acceptable salt thereof, can be formulated as an immediate release dosage form and the as-needed administering can range from about 1 minute to about 40 minutes prior to when the voiding and/or defecation is desired, from about 1 minute to about 20 minutes prior to when the voiding and/or defecation is desired, from about 1 minute to about 10 minutes prior to when the voiding and/or defecation is desired, or from about 1 minute to about 5 minutes prior to when the voiding and/or defecation is desired.

In one embodiment, one or more additional active agents or pudendal nerve blockade can be administered either simultaneously or sequentially with the peptide active agent in either a separate or a single formulation. The additional active agent may be one that is effective in treating bladder and/or bowel dysfunctions that accompany retention, such as overactive bladder or benign prostatic hyperplasia. The additional active agent may be one that potentiates the effect of the peptide active agent for treating bladder and/or bowel retention. Suitable additional active agents include, but are not limited to, for example, antimuscarinics (e.g. oxybutynin, solifenacin succinate, tolterodine), beta-3 adrenergic agonists (e.g. mirabegron), alpha adrenergic antagonists (e.g. silodosin, terazosin, tamsulosin, doxazosin, prazosin, alfuzosin), 5-alpha reductase inhibitors (e.g. finasteride, dutasteride), phosphodiesterase inhibitors (e.g. sildenafil, vardenafil, tadalafil) and/or any agent that does not inhibit the action of the primary active agent. Pudendal nerve blockade can be achieved pharmacologically through pharmaceutical agents that depress pudendal nerve reflexes, such as ethylketocyclazocine; or block pudendal nerve action potentials, such as local anesthetics (e.g. lidocaine). Pudendal nerve activity can also be blocked through high-frequency electrical stimulation of the pudendal nerve (e.g. >5 kHz, square wave pulses of current sufficient to activate pudendal motor neurons, with an equal on-off duty cycle).

The additional active agent may be a urethral relaxant agent such as, for example, an alpha adrenergic receptor blocker, a nitric oxide (NO) donor, a PDE5 inhibitor, or a Prostaglandin E receptor (EP1,2,3) agonist. The alpha adrenergic receptor blocker can be, for example, one of tamsulosin, silodosin, alfuzosin, or naftopidil or any other suitable alpha adrenergic receptor blocker. The NO donor can be, for example, one of sodium nitroprusside, glyceryltrinitrate, or S-nitrosothiol classes of NO donors or any other suitable NO donor. The PDE5 inhibitor can be, for example, one of sildenafil, tadalafil, vardenafil, avanafil, udenafil, dipyridamole, or vardenafil hydrochloride or any other suitable PDE5 inhibitor.

The additional active agent may be a compound that can induce one of colon contraction and/or sphincter relaxation in the subject. The anal sphincter relaxant agent can be, for example, one of vasoactive intestinal polypeptide (VIP), a NO donor, amyl nitrate, butyl nitrate, glyceryltrinitrate, an alpha adrenergic receptor blocker, tamsulosin, silodosin, alfuzosin, or naftopidilor other suitable anal sphincter relaxant agents.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March (1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other salts, enantiomers, analogs, esters, amides, prodrugs, active metabolites, and derivatives of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

The active agents of the present disclosure can be contained within a pharmaceutical formulation. The pharmaceutical formulation can be a unit dosage form. The pharmaceutical formulation can be selected from the group consisting of tablets, capsules, caplets, granules, beads, powders, pellets, liquid formulations, solutions, suspensions, syrups, suppositories, creams, ointments, pastes, gels, foams, and sprays.

The pharmaceutical formulation can be a tablet. The pharmaceutical formulation can be a rapidly disintegrating tablet. The tablet can be a rapidly disintegrating open matrix network tablet. The administration can be transmucosal and the rapidly disintegrating open matrix network tablet can include biodegradable polymers or ATRIX BEMA biodegradable polymers. The rapidly disintegrating open matrix network tablet can include biodegradable polymers or ATRIX BEMA biodegradable polymers.

The pharmaceutical formulation can be selected from the group consisting of suppositories, creams, ointments, liquid formulations, pastes, gels, foams, and sprays. The pharmaceutical formulation can be delivered through use of an iontophoresis, an electroporation, or a phonophoresis delivery mechanism. The pharmaceutical formulation can include a permeation enhancer.

The administration of the pharmaceutical formulation can be through a transdermal patch. The transdermal patch can include a permeation enhancer. The transdermal patch can include a needle free transdermal patch comprising electrical energy. The transdermal patch can include a needle free transdermal patch comprising microprojections.

The administration of the pharmaceutical formulation can be parenteral and can include an injection using an injection device.

Suitable compositions and dosage forms include tablets, capsules, caplets, pills, gel caps, troches, dispersions, suspensions, solutions, syrups, transdermal patches, gels, powders, magmas, lozenges, creams, pastes, plasters, lotions, discs, suppositories, liquid sprays for nasal or intraoral administration, dry powder or aerosolized formulations for inhalation, rapidly disintegrating tablets including effervescent tablets or wafers, ointments, liquid formulations, foams and the like. Further, those of ordinary skill in the art can readily deduce that suitable formulations involving these compositions and dosage forms, including those formulations as described elsewhere herein.

The present compositions may be administered intraorally, or placed within, and absorbed from, the oral cavity. For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

The dosage form may also be a rapidly disintegrating tablet, including an effervescent tablet or wafer. Examples of effervescent tablets may be found in the literature, and in, for example, U.S. Pat. No. 5,211,957 to Hagemann et al. Generally, effervescent tablets contain the active agent in combination with additives such as sodium bicarbonate and an organic acid. e.g., tartaric acid or citric acid. In the presence of water, these additives react to liberate carbon dioxide thereby facilitating the disintegration of the tablet. Once the tablet is substantially disintegrated, the active agent is absorbed through the oral mucosa thereby providing systemic adsorption of the active agent.

Another version of a rapidly disintegrating tablet includes "open matrix network" tablets. These tablets can disintegrate within seconds, i.e., within five to ten seconds, after being placed on the tongue of an individual. The contents of the tablet can then be swallowed with or without water. An example of such a tablet is found in U.S. Pat. No. 4,371,516 to Gregory et al. As described therein, the carrier provides a low density network, e.g., about 10 to about 200 mg/cm$^3$, of water-soluble or water-dispersible material. The tablet is produced by subliming a solution containing both the drug and carrier that is subsequently directed to a mold having tablet-shaped depressions. The carrier may be any suitable material, but is preferably gelatin, with partially hydrolyzed gelatin most preferred. Other examples of rapidly disintegrating tablets that can be adapted to contain active agents as discloses herein are well-known in the art. See, for example, U.S. Pat. No. 5,776,492 to Betzing et al.

Preferred buccal dosage forms will typically comprise a therapeutically effective amount of an active agent and a bioerodible (hydrolyzable) polymeric carrier that may also serve to adhere the dosage form to the buccal mucosa. The buccal dosage unit is fabricated so as to erode over a predetermined time period, wherein drug delivery is provided essentially throughout. The time period can be in the range of from about 1 minute to about 40 minutes, from about 1 minute to about 30 minutes, and from about 1 minute to about 10 minutes. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The "therapeutically effective amount" of the active agent in the buccal dosage unit will of course depend on the potency of the agent and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the active agent to be administered, and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (CARBOPOL, which may be obtained from B. F. Goodrich, is one such polymer). Other suitable polymers include, but are not limited to: hydrolyzed polyvinylalcohol; polyethylene oxides (e.g., SENTRY POLYOX water soluble resins, available from Union Carbide); polyacrylates (e.g., GANTREZ, which may be obtained from GAF); vinyl polymers and copolymers; polyvinylpyrrolidone; dextran; guar gum; pectins; starches; and cellulosic polymers such as hydroxypropyl methylcellulose, (e.g., METHOCEL, which may be obtained from the Dow Chemical Company), hydroxypropyl cellulose (e.g., KLUCEL, which may also be obtained from Dow), hydroxypropyl cellulose ethers (see, e.g., U.S. Pat. No. 4,704,285 to Alderman), hydroxyethylcellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., POLYPLASDONEXL, which may be obtained from GAF), cross-linked carboxylic methylcelluloses, such as croscarmelose (e.g., AC-DI-SOL, which may be obtained from FMC), alginic acid, and sodium carboxymethyl starches (e.g., EXPLOTAB, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., DI-TAB, which may be obtained from Stauffer), sugars that have been processed by cocrystallization with dextrin (e.g., co-crystallized sucrose and dextrin such as DI-PAK, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include tablets, creams, ointments, lozenges, pastes, and any other solid dosage form where the active ingredient is admixed into a disintegrable matrix. The tablet, cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units are fabricated to disintegrate rapidly. The time period for complete disintegration of the dosage unit is typically in the range of from about 10 seconds to about 30 minutes, and optimally is less than 5 minutes.

Other components may also be incorporated into the sublingual and lingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylenesorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art.

Preferred transrectal dosage forms include rectal suppositories, creams, ointments, and liquid formulations (enemas). The suppository, cream, ointment or liquid formulation for transrectal delivery comprises a therapeutically effective amount of the selected active ingredient and one or more conventional nontoxic carriers suitable for transrectal drug administration. The transrectal dosage forms of the present invention can be manufactured using conventional processes.

The active agents may also be administered intranasally or by inhalation. Compositions for intranasal administration are generally liquid formulations for administration as a spray or in the form of drops, although powder formulations for intranasal administration, e.g., insufflations, are also known, as are nasal gels, creams, pastes or ointments. For liquid formulations, the active agent can be formulated into a solution, e.g., water or isotonic saline, buffered or unbuffered, or as a suspension. Preferably, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, simply by way of example, phosphate buffers. Furthermore, various devices are available in the art for the generation of drops, droplets and sprays, including droppers, squeeze bottles, and manually and electrically powered intranasal pump dispensers. Active agent containing intranasal carriers may also include nasal gels, creams, pastes or ointments with a viscosity of, e.g., from about 10 to about 6500 cps, or greater, depending on the desired sustained contact with the nasal mucosal surfaces. Such carrier viscous formulations may be based upon, simply by way of example, alkylcelluloses and/or other biocompatible carriers of high viscosity well known to the art. Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitanmonopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of from about 0.1 μm to about 50 μm, from about 1 μm to about 25 μm.

Topical formulations may be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. Ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glycerylmonostearate, lanolin and stearic acid. Preferred water-soluble ointment bases are prepared from polyethylene glycols of varying molecular weight.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the CARBOPOL trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed above in transmucosal compositions.

In one embodiment of the present disclosure, the active agent is administered transdermally. The transdermal administration can include use of a transdermal patch. The transdermal patch can include a permeation enhancer. The transdermal patch can include a needle free transdermal patch that includes use of electrical energy. The needle free transdermal patch that includes use of electrical energy can be VYTERIS SMART PATCH DRUG DELIVERY. The transdermal patch can include a needle free transdermal patch having microprojections. The needle free transdermal patch having microprojections can be ZP PATCH TECHNOLOGY. The needle free transdermal patch can be a V-GO patch.

Parenteral administration, if used, is generally characterized by injection, including intramuscular, intraperitoneal, intravenous (i.v.) and subcutaneous injection. Injectable formulations can be prepared in conventional forms, either as liquid solutions or suspensions; solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

One of skill in the art recognizes that the concentration of the active agent in any of the aforementioned dosage forms and compositions can vary a great deal and will depend on a variety of factors, including the type of composition or dosage form, the corresponding mode of administration, the nature and activity of the specific active agent, and the intended drug release profile. Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration.

The unit dose for intraoral administration of the individual active agents (SEQ ID NOs: 1-11) can be in the range of from about 1 nanogram (ng) to about 10,000 mg, in the range of from about 100 ng to about 5,000 mg; and for local administration, suitable unit doses may be lower. The unit dose for intraoral administration can be greater than about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg.

For individual active agents (SEQ ID NOs: 1-11), the unit dose for transmucosal, topical, transdermal, and parenteral administration can be in the range of from about 1 ng to about 10,000 mg, in the range of from about 100 ng to about 5,000 mg. The unit dose for transmucosal, topical, transdermal, and parenteral administration can be greater than about 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 .µg, about 20 µg, about 30 µg, about 40 µg, about 50 µg, about 100 µg, about 200 µg, about 300 µg, about 400 µg, about 500 µg, about 1 mg, about 5 mg, about 10 mg, about 20 mg, about 30 mg, about 40 mg, about 50 mg, about 100 mg, about 200 mg, about 300 mg, about 400 mg, about 500 mg, about 1,000 mg, about 1,500 mg, about 2,000 mg, about 2,500 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg.

A therapeutically effective amount of a particular active agent administered to a given individual will, of course, be dependent on a number of factors, including the concentration of the specific active agent, composition or dosage form, the selected mode of administration, the age and general condition of the individual being treated, the severity of the individual's condition, and other factors known to the prescribing physician. However, one of skill in the art would readily recognize that the therapeutically effective amount of a particular active agent must be selected so as to allow for as-needed administration, as defined further herein.

With an immediate release dosage form, as-needed administration may involve drug administration immediately prior to when commencement of emptying of the bladder or bowel would be desirable. The as-need administration can range from about 1 minute to about 40 minutes prior to the desired emptying, from about 1 minute to about 20 minutes prior, from about 1 minute to about 10 minutes prior, or about 1 minute to about 5 minutes prior.

In another embodiment, a packaged kit is provided that contains the pharmaceutical formulation to be administered, i.e., a pharmaceutical formulation containing a therapeutically effective amount of a individual active agent selected from SEQ ID NOs: 1-11, or a pharmaceutically acceptable salt thereof, for the treatment of loss of or decrease in voluntary control of voiding and/or defecation or having urinary and/or fecal incontinence, a container, preferably sealed, for housing the formulation during storage and prior to use, and instructions for carrying out drug administration in a manner effective to treat the loss or decrease in control and/or the incontinence. The instructions will typically be written instructions on a package insert and/or on a label. Depending on the type of formulation and the intended mode of administration, the kit may also include a device for administering the formulation. The formulation may be any suitable formulation as described herein. The manner for treating the loss of or decrease in voluntary control of voiding and/or defecation or having urinary and/or fecal incontinence may be administration on an as-needed basis to treat the urinary voiding and/or defecation dysfunction. The as-need basis can range from about 1 minute to about 40 minutes prior to when the voiding and/or defecation is desired, from about 1 minute to about 20 minutes prior to when the voiding and/or defecation is desired, from about 1 minute to about 10 minutes prior, or from about 1 minute to about 5 minutes prior to when the voiding and/or defecation is desired.

The kit may contain multiple formulations of different dosages of the same agent. The kit may also contain multiple formulations of different active agents. The kit may contain formulations suitable for sequential, separate and/or simultaneous use in the treatment of urinary voiding and/or defecation dysfunction, and instructions for carrying out drug administration where the formulations are administered sequentially, separately and/or simultaneously in the treatment of urinary voiding and/or defecation dysfunction. The parts of the kit may be independently held in one or more containers—such as bottles, syringes, plates, wells, blister packs, or any other type of pharmaceutical packaging.

The packaged kit may further comprise a therapeutically effective amount of a NK2R antagonist, or a pharmaceutically acceptable salt thereof, to terminate the majority of the effects of the peptide selected from SEQ ID NOs: 1-11 within about 10 minutes, wherein the NK2R antagonist has a duration of action of less than about 4 hours. The NK2R antagonist can have a duration of action of less than about 3 hours. The NK2R antagonist can have a duration of action of less than about 2 hours.

In the packaged kit, the peptide and the NK2R antagonist can be formulated together in a single pharmaceutical formulation and an onset of action of the NK2R antagonist can be longer than the onset of the peptide. The onset of action of the NK2R antagonist can be longer than the onset of the peptide to terminate the majority of the effects of the peptide within about 5 minutes. The onset of action of the NK2R antagonist can be longer than the onset of the peptide to terminate the majority of the effects of the NK2R agonist within about 10 minutes.

In the packaged kit, the peptide and the NK2R antagonist can be formulated separately in two separate pharmaceutical formulations, wherein the NK2R antagonist is administered subsequent to administration of the peptide, and wherein an onset of action of the NK2R antagonist can range from about 1 to about 10 minutes. The onset of action of the NK2R antagonist can range from about 1 to about 5 minutes.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Heptapeptide Analogs of NKA: Associated Purity and Saline Solubility

Heptapeptides A-K shown below in Table 1 (SEQ ID NOs: 1-11) were synthesized according to standard Fmoc-mediated solid-phase techniques and purified under typical C18 reverse-phase conditions.

TABLE 1

| SEQ ID NO: | Cmpd | Sequence | HPLC Purity | [M + H]+ | Saline Solubility (mg/mL) |
|---|---|---|---|---|---|
| 1 | A | Asp-Lys-Phe-Val-Gly-(NMe-Leu)-Met-NH2 | 98 | 820 | ≥20 |
| 2 | B | Asp-Arg-Phe-Val-Gly-(NMe-Leu)-Nle-NH2 | 99 | 832 | ≥20 |
| 3 | C | Asp-Arg-Phe-Val-Gly-(NMe-Leu)-Met-NH2 | 98 | 850 | ≥20 |
| 4 | D | Asp-Lys-Phe-Val-Gly-Leu-Met-NH2 | 95 | 808 | <1 |
| 5 | E | Asp-Lys-Phe-Val-(β-Ala)-Leu-Met-NH2 | 96 | 822 | <1 |
| 6 | F | Asp-Lys-Phe-Val-Gly-Leu-Nle-NH2 | 95 | 790 | <1 |
| 7 | G | Asp-Lys-Phe-Val-(β-Ala)-Leu-Nle-NH2 | 99 | 804 | <1 |
| 8 | H | Asp-Arg-Phe-Val-Gly-Leu-Met-NH2 | 96 | 836 | <1 |
| 9 | I | Asp-Arg-Phe-Val-(β-Ala)-Leu-Met-NH2 | 99 | 850 | <1 |
| 10 | J | Asp-Arg-Phe-Val-Gly-Leu-Nle-NH2 | 99 | 818 | <1 |
| 11 | K | Asp-Arg-Phe-Val-(β-Ala)-Leu-Nle-NH2 | 97 | 832 | <1 |

Heptapeptide analogs of NKA were synthesized to >95% purity. Compounds A (SEQ ID NO: 1), B (SEQ ID NO: 2), and C (SEQ ID NO: 3) exhibited saline solubility >20 mg/mL. Compounds D-K were considered to be insoluble in saline (<1 mg/mL).

Example 2

In Vitro Receptor Binding Affinities

Radioligand competition binding assays were performed to determine the receptor affinities and selectivity of the compounds A-K shown in Table 1 (SEQ ID NOs: 1-11) for human NK2 Receptor (hNK2R) and human NK1 Receptor (hNK1R).
Methods Cell Lines: Human recombinant NK2 and NK1 receptors were generated using stably transfected CHO cells (CHO-hNK2 and CHO-hNK1, respectively). Human NK2 or NK1 receptor expressing vectors from Genecopeia (Rockville, USA) were transfected in CHO cells using the standard FuGENE protocol and cells were selected using 450 μg/mL geneticin (G418). Clones expressing the receptors were selected by functional coupling to calcium using FLIPR and a single clone for each receptor subtype was selected for expansion and stable cell line generation. Cells were cultured in a humidified incubator with 5% CO2 in F12K medium containing 10% heat inactivated FBS and 450 μg/mL geneticin and passaged on reaching 80-90% confluence.

Membrane Preparation: Protein expression was induced by addition of 5 mM sodium butyrate to the culture medium. After 16 h, the medium was removed and the cells were washed with PBS (calcium and magnesium-free) and detached. The cell suspension was collected, maintained on ice and centrifuged for 5 min at 4° C. and 1200 rpm in a Beckman GS6R centrifuge. After removal of the supernatant the cell pellet was washed and collected by re-suspension in PBS and centrifugation. The final pellet was weighed and frozen at −80° C. until use.

Frozen pellets were thawed and homogenized in 10 volumes (w/v) of membrane preparation buffer (50 mM HEPES pH 7.4, 1 mM EDTA, 50 μg/mL bacitracin and protease inhibitors) using a Polytron Ultraturrax (twice for 15 s per cycle). The homogenate was centrifuged for 20 min at 4° C. and 18500 rpm in a SL-50T Sorvall rotor and the pellet was re-suspended in membrane preparation buffer and re-homogenized as before. After centrifugation for 20 min at 4° C. and 18500 rpm, the pellets were re-suspended in 5 volumes of membrane preparation buffer and divided into aliquots before freezing at −80° C. Protein concentration was determined using BioRad Protein Assay (Milan, Italy) with a BSA standard curve.

Filtration Assays: Stock solutions of compounds (10 mM) were prepared in DMSO and stored at −20° C. until use. Further dilutions were performed in DMSO to provide an 11-point concentration response curve (CRC) spanning final concentrations from 0.01 nM to 10 μM. Radioligand binding experiments were performed immediately after transferring 2 μL of each concentration of test compound to a 96-well plate. Each well contained a final volume of 200 μL buffer (50 mM HEPES, 3 mM MnCl2, 0.02% BSA, 0.02% Pluronic F-127 and 50 μg/mL bacitracin, pH 7.4). All reactions (except for [3H]-septide saturation curve) were stopped by rapid filtration through Unifilter-96 GF/C filter plates pre-soaked for one hour in 0.5% PEI followed by 3 washings with 1 mL ice-cold 0.9% NaCl using a Packard cell Harvester. After drying for 1 h at 40° C., 50 μL of Microscint-20 was added to each filter plate and bound radioactivity was measured using a Microplate TopCount (Packard C9912). [3H]-septide saturation reactions were terminated by rapid filtration through GF/B filter paper pre-soaked in PEI 0.5% (w/v) solution and washed with 1 mL of ice cold 0.9% NaCl before filtration on a Brandel Harvester. Filters were washed 4 times with 1 mL ice cold 0.9% NaCl and placed into pico vials with 4 mL of Filter Count.

The radioligand concentration was determined by measurement of 50 μL of [125I]-NKA, or 100 μL of [3H]-septide, mixed with 3 mL of Filter Count using a β-Counter TriCarb 2900.

[125I]-NKA Binding to Human Recombinant NK2Rs: 100 μL of [125I]-NKA (PERKIN ELMER, USA, specific activity 81.4 TBq/mmol) was incubated with 100 μL of the CHO-hNK2 membrane suspension under the following conditions: to determine protein linearity, 0.1 nM [125I]-NKA was incubated with increasing concentrations of CHO-hNK2 membranes (1, 3, 10 and 30 µg/well) at 23° C. for 2 h; to examine association kinetics, 0.1 nM [125I]-NKA was incubated with CHO-hNK2 membranes (6 µg/well) at 23° C. for a range of durations from 10 to 240 min; in the saturation study, final concentrations of [125I]-NKA and NKA from 0.02 to 5 nM (1 part hot/4 parts cold) were incubated with CHO-hNK2 membranes (6 µg/well) at 23° C. for 3 h; in competition binding experiments, test compounds were incubated with 0.1 nM [125I]-NKA and CHO-hNK2 membranes (6 µg/well) at 23° C. for 3 h.

Total binding was defined by the addition of 2 µL DMSO, and nonspecific binding was defined by the addition of 2 µL of 100 µM NKA (1 µM final concentration).

[3H]-septide Binding to Human Recombinant NK1Rs: 100 µL of [3H]-septide (QUOTIENT BIORESEARCH, UK, specific activity 3.9 TBq/mmol) was incubated with 100 µL of CHO-hNK1 membrane suspension under the following conditions: to determine protein linearity, 4 nM [3H] septide was incubated with increasing concentrations of CHO-hNK1 membranes (10, 15, 20, 25 and 30 µg/well) at 23° C. for 90 min; to examine association kinetics, 5 nM [3H]-septide was incubated with CHO-hNK1 membranes (17 µg/well) at 23° C. for a range of durations from 2 to 120 min in the saturation study, final concentrations of [3H]-septide from 0.1 to 100 nM were incubated with CHO-hNK1 membranes (20 µg/well) at 23° C. for 2 h; in competition binding experiments, test compounds were incubated with 5.0 nM [3H]-septide and CHO-hNK1 membranes (20 µg/well) at 23° C. for 1 h. Total binding was defined by the addition of 2 µL of DMSO, and nonspecific binding was defined by the addition of 2 µL of 100 µM septide (1 µM final concentration).

Results

Displacement of [125I]-NKA Binding to Human NK2Rs: Displacement curves for 11 heptapeptide analogs of NKA are shown in FIGS. 1A-1K. Most Hill slopes approached unity, ranging from −0.8 to −0.9. For calculation of the affinity constant (Ki), curve fitting was modeled to a single site. All test compounds competed for [125I]-NKA binding to hNK2Rs, with Compounds C (SEQ ID NO: 3) and A (SEQ ID NO: 1) demonstrating the highest affinity, and Compounds K (SEQ ID NO: 11) and G (SEQ ID NO: 7) demonstrating the lowest affinity for hNK2Rs (see Table 2).

Displacement of [3H] septide Binding to Human NK1Rs: Displacement curves for 11 heptapeptide analogs of NKA are shown in FIGS. 2A-2K. Most Hill slopes approached unity, ranging from −0.8 to 1.1. For calculation of Ki, curve fitting was modeled to a single site. All compounds competed for [3H] septide binding to hNK1Rs, with Compounds H (SEQ ID NO: 8) and D (SEQ ID NO: 4) demonstrating the highest affinity, and Compounds K (SEQ ID NO: 11) and G (SEQ ID NO: 7) demonstrating the lowest affinity for hNK1Rs (Table 2).

TABLE 2

Summary of binding affinities for human NK2Rs and NK1Rs

| SEQ ID NO: | Cmpd | Sequence | hNK2 binding Ki (nM) | hNK1 binding Ki (nM) | hNK2 selectivity ratio |
|---|---|---|---|---|---|
| 1 | A | Asp-Lys-Phe-Val-Gly-(NMe-Leu)-Met-NH2 | 0.20 | 50.12 | 248.89 |
| 2 | B | Asp-Arg-Phe-Val-Gly-(NMe-Leu)-Nle-NH2 | 0.59 | 331.13 | 557.83 |
| 3 | C | Asp-Arg-Phe-Val-Gly-(NMe-Leu)-Met-NH2 | 0.12 | 20.89 | 167.49 |
| 4 | D | Asp-Lys-Phe-Val-Gly-Leu-Met-NH2 | 0.38 | 15.85 | 41.64 |
| 5 | E | Asp-Lys-Phe-Val-(β-Ala)-Leu-Met-NH2 | 2.11 | 257.04 | 122.04 |
| 6 | F | Asp-Lys-Phe-Val-Gly-Leu-Nle-NH2 | 2.75 | 223.87 | 81.47 |
| 7 | G | Asp-Lys-Phe-Val-(β-Ala)-Leu-Nle-NH2 | 16.39 | 3090.30 | 188.58 |
| 8 | H | Asp-Arg-Phe-Val-Gly-Leu-Met-NH2 | 0.31 | 8.32 | 27.10 |
| 9 | I | Asp-Arg-Phe-Val-(β-Ala)-Leu-Met-NH2 | 0.88 | 95.50 | 108.27 |
| 10 | J | Asp-Arg-Phe-Val-Gly-Leu-Nle-NH2 | 1.74 | 125.89 | 72.53 |
| 11 | K | Asp-Arg-Phe-Val-(β-Ala)-Leu-Nle-NH2 | 6.85 | 1202.26 | 175.59 |

All compounds exhibited a >20-fold selectivity for hNK2R binding compared to hNK1R binding. Compounds C (SEQ ID NO: 3), K (SEQ ID NO: 11), G (SEQ ID NO: 7), A (SEQ ID NO: 1) and B (SEQ ID NO: 2) exhibited the greatest selectivity for hNK2Rs (>150-fold selectivity).

Example 3

In Vitro Functional Activity

Although in vitro binding assays provide affinity and binding selectivity information, it is important to determine if compounds produce functional activation of receptors. As a comparison to binding studies, a series of experiments were conducted to evaluate intracellular calcium mobilization produced during in vitro activation of hNK2R and hNK1Rs by heptapeptide analogs.

Methods

Intracellular Calcium Mobilization: The agonist efficacy of heptapeptide analogs of NKA at recombinant hNK1R or hNK2Rs expressed in CHO cells was assessed by measuring intracellular calcium mobilization using the calcium-sensitive dye Fluo-4 AM (MOLECULAR PROBES, EUGENE, Oreg., USA) and a Fluorometric Imaging Plate Reader (FLIPR, MOLECULAR DEVICES, CA, USA). CHO-hNK1 and CHO-hNK2 cells were seeded into black walled clear-bottom 384-well plates) at a density of 10,000 and 15,000 cells per well in 50 µL culture media, respectively, and grown overnight at 37° C. in a humidified CO2-incubator. Cells were washed in washing buffer using the EMBLA 384 instrument, leaving 20 µL of buffer per well after the final aspiration. Cells were then incubated at 37° C. with the cytoplasmic Ca2+ indicator Fluo-4 AM (final concentration 1 µM) in assay buffer (20 mM HEPES, 145 mM NaCl, 5 mM KCl, 5.5 mM glucose, 1 mM MgCl2 and 2 mM CaCl2, pH 7.4, 0.05% Pluronic F-127 and 0.1% BSA) containing 2.5 mM probenecid for 45-60 min (cell loading). Cells were then washed 3 times in washing buffer (20 mM HEPES, 145 mM NaCl, 5 mM KCl, 5.5 mM glucose, 1 mM MgCl2 and 2 mM CaCl2, pH 7.4 and 2.5 mM probenecid) using the EMBLA 384 instrument, leaving 30 µL of buffer in each well after the last wash. Loaded cell plates were transferred to the FLIPR machine and calcium responses were monitored as described below. A dual read-out FLIPR protocol was used, allowing for characterization of both agonist and antagonist profiles. For quality control, in each compound plate the signal was monitored by evaluating the responses to the reference standards (NKA and Substance P).

Agonist Effect on Calcium Mobilization: Eleven concentrations of the compounds were evaluated for their ability to increase intracellular calcium levels with respect to the agonist reference standard (NKA or Substance P), and the EC50 value was calculated. The range of final concentrations tested was 0.169 nM to 10 µM, or 1.69 pM to 100 nM, depending on compound potency. Concentration response curves of compounds were run in duplicate on two different occasions from the same stock solutions. Test solutions were prepared from 10 mM stock solutions in DMSO and 1 µL of each solution was stamped into V-bottom assay plates containing 49 µL assay buffer. The final concentration of DMSO was 0.5% in each well.

Results

Intracellular Calcium Mobilization:

NK2Rs: All compounds elicited concentration-dependent calcium responses (FIGS. 3A-3K) and were full agonists at the hNK2R (>80% maximal response compared to Neurokinin A). Compounds B (SEQ ID NO: 2) and D (SEQ ID NO: 4) were the most potent and Compounds K (SEQ ID NO: 11) and G (SEQ ID NO: 7) the least potent (see Table 3).

NK1Rs: All compounds elicited concentration-dependent calcium responses (FIGS. 3A-3K) and were full agonists at the hNK1R (>90% maximal response compared to Substance P). Compounds H (SEQ ID NO: 8) and C (SEQ ID NO: 3) were the most potent and Compounds K (SEQ ID NO: 11) and G (SEQ ID NO: 7) the least potent (see Table 3).

NK2R/NK1R ratio: The ratios of EC50s for hNK1R/hNK2R reveal the selectivity for activation of hNK2Rs vs hNK1Rs. Table 3 shows that Compounds K (SEQ ID NO: 11), G (SEQ ID NO: 7), E (SEQ ID NO: 5) and B (SEQ ID NO: 2) exhibited the greatest selectivity as they were all >20-fold more selective for hNK2Rs in this assay.

TABLE 3

Summary of in vitro functional potency at human NK2Rs and NK1Rs.

| SEQ ID NO: | Compound | Sequence | hNK2 EC50 (nM) | hNK1 EC50 (nM) | hNK2 selectivity ratio |
|---|---|---|---|---|---|
| 1 | A | Asp-Lys-Phe-Val-Gly-(NMe-Leu)-Met-NH2 | 0.14 | 0.95 | 7 |
| 2 | B | Asp-Arg-Phe-Val-Gly-(NMe-Leu)-Nle-NH2 | 0.08 | 5.84 | 70 |
| 3 | C | Asp-Arg-Phe-Val-Gly-(NMe-Leu)-Met-NH2 | 0.16 | 0.3 | 2 |
| 4 | D | Asp-Lys-Phe-Val-Gly-Leu-Met-NH2 | 0.09 | 0.41 | 5 |
| 5 | E | Asp-Lys-Phe-Val-(β-Ala)-Leu-Met-NH2 | 0.18 | 6.31 | 36 |
| 6 | F | Asp-Lys-Phe-Val-Gly-Leu-Nle-NH2 | 0.38 | 2.36 | 6 |
| 7 | G | Asp-Lys-Phe-Val-(β-Ala)-Leu-Nle-NH2 | 3 | 78.22 | 26 |
| 8 | H | Asp-Arg-Phe-Val-Gly-Leu-Met-NH2 | 0.19 | 0.16 | 0.8 |
| 9 | I | Asp-Arg-Phe-Val-(β-Ala)-Leu-Met-NH2 | 0.15 | 1.83 | 12 |
| 10 | J | Asp-Arg-Phe-Val-Gly-Leu-Nle-NH2 | 0.2 | 1.71 | 9 |
| 11 | K | Asp-Arg-Phe-Val-(β-Ala)-Leu-Nle-NH2 | 1.16 | 29.51 | 25 |

All compounds were full agonists for both hNK2Rs and hNK1Rs in this assay. Ten of eleven compounds demonstrated selectivity for hNK2Rs with Compounds K (SEQ ID NO: 11), G (SEQ ID NO: 7), E (SEQ ID NO: 5) and B (SEQ ID NO: 2) identified as the most selective.

Example 4

Pharmacokinetics in Rat

The concentrations of compounds (SEQ ID NOS: 1-11) were measured in rat plasma after intravenous (IV) bolus dosing to determine pharmacokinetic profiles of individual compounds.

Methods

Animal preparation: In vivo studies were performed in anesthetized adult Sprague Dawley rats. Rats were anesthetized with urethane (1.2-1.4 g/kg subcutaneous injection).

Surgical procedures were then performed with the addition of isoflurane anesthesia (0.05-1.5% in 02) as needed. A venous cannula was inserted into the jugular vein for intravenous (IV) administration of compounds.

In vivo dosing and plasma sampling: Compounds were divided into two groups (soluble and insoluble). Each group was dosed as a cassette in which four compounds (100 µg/kg each compound) were combined into a single IV bolus injection to anesthetized adult Sprague-Dawley rats. Soluble compounds were dissolved in saline. Insoluble compounds were dissolved in a 10% ethanol/saline solution. Rats were cassette dosed based on weight using 0.1 mg/mL solutions of individual compounds. Blood samples (700 µL) were collected using a carotid artery cannula into EDTA tubes containing ascorbic acid (final concentration 1%), and plasma was isolated.

Bioanalytical assay: A reversed-phase HPLC with Turbo Ion Spray MS/MS detection method was developed for bioanalysis. Mass spec transition and settings were individually optimized for each compound and then compounds were cassetted for HPLC method development and optimization. [$^{13}C_9$; $^{15}N$] [Lys5,MeLeu9,Nle10]-NKA(4-10) was used as an internal standard (IS). Analyte-to-IS peak area ratios for individual compounds were used to create linear calibration curves (1-20 ng/mL) using 1/×2 weighted least-squares regression analysis for evaluation of method linearity, precision and accuracy. For plasma concentration measurements, plasma samples were spiked with IS, processed by extraction, and analyzed using LC-MS/MS. Positive (M+H)+ ions for individual compounds and IS were monitored in MRM mode.

Figure 4A:
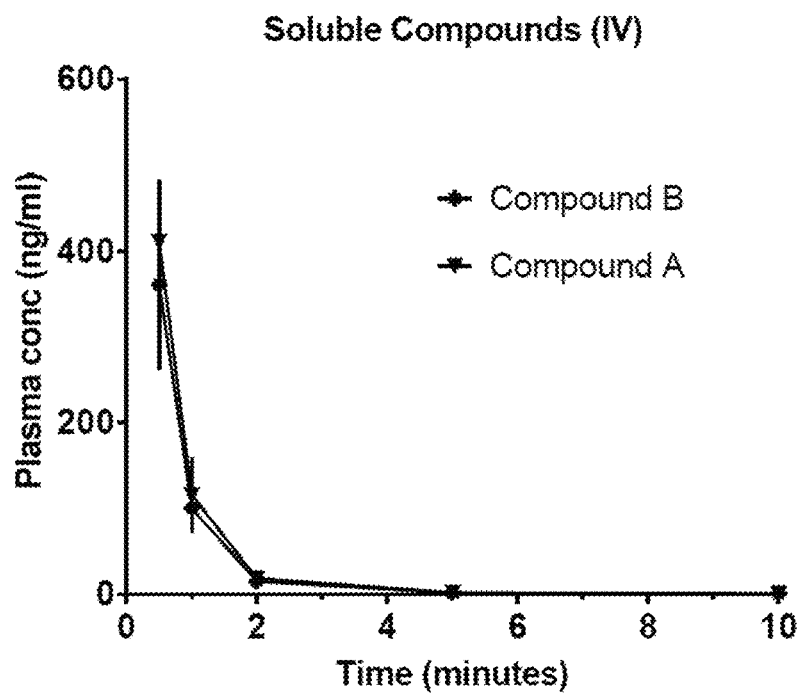
FIG. 4A is a graph showing comparison of PK profiles following cassette intravenous (IV) dosing of rats with soluble heptapeptide analogs A (SEQ ID NO: 1) and B (SEQ ID NO: 2) dissolved in saline according to one or more embodiments of the invention.
Figure 4B:
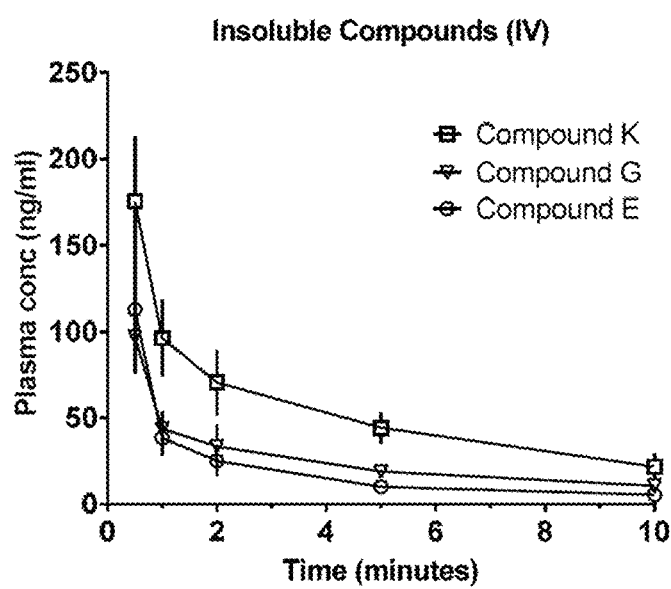
FIG. 4B is a graph showing comparison of PK profiles following cassette intravenous (IV) dosing of rats with insoluble heptapeptide analogs K (SEQ ID NO: 11), G (SEQ ID NO: 7) and E (SEQ ID NO: 5) dissolved in a 10% ethanol/saline solution according to one or more embodiments of the invention.

Results: FIGS. 4A and 4B show a comparison of the PK profiles of selected compounds from two cassettes following IV bolus dosing. IV cassette doses of (FIG. 4A) 4 soluble compounds and (FIG. 4B) 4 insoluble compounds were administered to, and plasma samples collected from, N=2 male+2 female rats per cassette. The maximal mean plasma concentrations of all compounds were >100 ng/mL, indicating successful dose administration and detection. Soluble compounds were dissolved in saline and insoluble compounds dissolved in a 10% ethanol/saline solution. All compounds were visibly in solution at the doses administered. Plasma concentrations of two soluble compounds (FIG. 4A) decreased rapidly ($t_{1/2}$=0.2-1.2 min) to levels <1 ng/mL by 10 min post-dose. In addition, plasma concentrations of four insoluble compounds (FIG. 4B) also decreased rapidly ($t_{1/2}$=3.3-4.7 min). These data demonstrate that individual compounds demonstrate rapid pharmacokinetics with fast plasma half-lives of <5 min.

Example 5

In Vivo Pharmacodynamics in Rat

Individual compound B (SEQ ID NO: 2) was administered to rats to evaluate effects on bladder and bowel activity and to demonstrate efficacy following SC dosing.

Methods: Studies were conducted in acutely spinal transected rats under isovolumetric bladder pressure recording conditions. Acute spinal cord injury (aSCI) is an in vivo model of isolated bladder smooth muscle contraction without reinforcement from micturition reflexes (i.e., myogenic, not neurogenic, contraction). Thus, it can be viewed as a model of severe bladder underactivity.

Animal preparation: In vivo studies were performed in anesthetized, acutely spinalized (T8-10 level) rats. Rats were anesthetized with urethane (1.2-1.4 g/kg subcutaneous injection). Surgical procedures were then performed with the addition of isoflurane anesthesia (0.05-1.5% in 02) as needed.

For aSCI, the skin and muscle on the dorsal side at the level of the lower thoracic vertebrae were incised and the spinal cord was carefully exposed by a laminectomy and transected at the T8-T10 spinal level. Gelfoam was placed at the incision site and the muscle and skin overlying the vertebrae were closed with wound clips. The spinal cord was cut at least 60 min before starting the experimental protocol. Bladder pressure and colorectal (/bowel) pressure signals were amplified and displayed on a computer using LABCHART (AD Instruments, Colorado Springs, Colo.).

Bladder Contractility: For isovolumetric recordings of bladder pressure, saline-filled polyethylene tubing with a flared tip (PE 50) catheter was inserted into the bladder and secured in place at the dome. This catheter was used to slowly infuse saline (0.2-0.3 ml/min by an infusion pump (PHD2000 INFUSION, HARVARD Apparatus, Holliston, Mass.) to determine the bladder capacity. The bladder capacity was determined as the volume necessary to fill the bladder to the leak point pressure (i.e. volume required to produce voiding). The bladder was then emptied, the external urethra occluded and the bladder filled to 70% capacity. This method produced a stable baseline pressure in which drug-induced changes in bladder contractility could be measured. Peak pressure responses, time to peak, and time to return to near baseline values (within 5 mmHg of baseline; i.e. duration of action) after vehicle and drug administration were measured.

Bowel Contractility: Colorectal pressure manometry was performed via a latex balloon catheter (length 3-5 cm) inserted (~4 cm) into the distal rectal/colon region. The catheter was connected to a pressure monitoring system. The pressure in the balloon catheter was slowly increase to 15-20 mmHg by infusing saline (0.3-0.7 ml total volume) and this pressure was maintained throughout the study. This allowed drug induced changes in colorectal pressure to be monitored. Parameters measured include peak colorectal pressure response, duration of time above baseline activity (in the $1^{st}$ 5 min after drug administration), area under the curve (measured during the $1^{st}$ 5 min after drug administration) and the number of contractile events after vehicle and drug administration.

Dosing: Compound B (SEQ ID NO: 2) was dissolved in saline and subcutaneous doses were administered in a dose range of 1-300 µg/kg.

Data analysis: Data were examined qualitatively and quantitatively. The mean, standard deviation and standard error of the mean were calculated using MICROSOFT EXCEL.

Results: FIG. 5 illustrates the pharmacodynamics of Compound B (SEQ ID NO: 2), specifically, a physiograph tracing showing a rapid dose-related increase in bladder pressure after consecutive injections of Compound B (SEQ ID NO: 2) (1-100 µg/kg SC, indicated by each arrow) in an anesthetized aSCI rat. The duration of action at the maximal dose tested was 15 to 30 min. SC administration of Compound B (SEQ ID NO: 2) (N=3 male+3 female) evoked a dose related, fast onset (<2 min) increase in bladder contraction pressure (see FIG. 5). FIGS. 6A and 6B show dose related increase in bladder (6A) and bowel (6B) activity after consecutive SC administrations of Compound B (SEQ ID NO: 2) in the acute SCI rat. Data are mean+SD of peak bladder pressure (A) and bowel pressure AUC for the first 5 min after each dose (B). N=4-6 for all doses. At doses >10 µg/kg SC, Compound B (SEQ ID NO: 2) produced measurable increases in bladder activity (see FIG. 6A). At doses >10 µg/kg SC, Compound B (SEQ ID NO: 2) produced measurable increases in bowel activity (see FIG. 6B).

These data demonstrate that Compound B (SEQ ID NO: 2) induces a fast onset, short duration bladder contraction, and dose-related increases in both bladder and bowel pressure following SC dose administration.

Example 6

In Vivo Pharmacodynamics in Dog

Individual compounds B (SEQ ID NO: 2), E (SEQ ID NO: 5) and G (SEQ ID NO: 7) were administered to dogs to evaluate effects on bowel activity and to demonstrate efficacy following IV and SC dosing.

Methods

Animal preparation: Naïve beagle dogs were fasted for 12-24 hours and received a warm water enema the night prior to, and the morning of, the experiment to clear the rectum and lower colon of feces. The day of the experiment, a 20 gauge IV catheter (Terumo Surflo) was placed in the cephalic vein for anesthetic induction (propofol, 10 mg/kg; IV) and delivery of IV fluids (5-10 ml/kg/hr) and compounds. The sedated dog was intubated with a 5-6 Fr tracheal tube and was maintained on 2-3% isoflurane via a ventilator (15-25 breaths/min; tidal volume 120-140 mmHg) for the remainder of the experiment.

Bowel contractility: For colorectal pressure manometry, an ~3 inch balloon catheter was inserted into the rectum and secured to the tail with tape. This catheter was connected via a three-way stopcock to a pressure transducer (UTAH MEDICAL PRODUCTS; DelTran II) for pressure recording. Data were recorded using PowerLab/8SP acquisition system using LabChart software (version 7.3.7; ADINSTRUMENTS, Australia). Arterial pressure, ECG, temperature and blood oxygen saturation (spO2) were monitored throughout the experiment (MEDTRONIC LIFEPAK12). Dogs were recovered in a quiet room under veterinary supervision.

Studies were conducted in accordance with an approved IACUC protocol and The Guide for the Care and Use of Laboratory Animals, published by the Institute of Laboratory Animal Resources, Commission on Life Science, National Research Council, Eighth Edition and applicable USDA regulations.

Results

Compound B-induced bowel contractions: Compound B (SEQ ID NO: 2) was dissolved in saline and administered as an IV bolus injection (3 µg/kg) or SC injection (30 µg/kg). FIG. 7 shows a physiograph trace of colorectal pressure recorded from an anesthetized dog. Both IV and SC doses of Compound B (SEQ ID NO: 2) produced a rapid (within 3 minutes) increase in colorectal pressure. The response to IV dosing lasted approximately 7 minutes and the SC dose lasted over 30 minutes. Both doses produced leakage of urine from the bladder consistent with increase bladder pressures and induction of voiding (data not shown).

Compound E-induced bowel contractions: Compound E (SEQ ID NO: 5) was dissolved in 50% DMSO in saline and administered as an IV bolus injection (3 ug/kg). FIG. 8 shows a physiograph trace of colorectal pressure recorded from an anesthetized dog. An IV dose of Compound E (SEQ ID NO: 5) produced a rapid (within 1 minute) increase in colorectal pressure. The response to IV lasted approximately 4 minutes. Control solutions of 50% DMSO in saline produced no colorectal responses (data not shown).

Compound G-induced bowel contractions: Compound G (SEQ ID NO: 7) was dissolved in 50% DMSO in saline and administered as an IV bolus injection. FIG. 9 shows a physiograph trace of colorectal pressure recorded from an anesthetized dog. IV doses of Compound G (SEQ ID NO: 7) produced dose-related, rapid (within 1 minute) increases in colorectal pressure. The responses to IV doses of 3, 30 and 66 ug/kg all lasted approximately 5 minutes. Control solutions of 50% DMSO in saline produced no colorectal responses (data not shown).

These data demonstrate that Compounds B (SEQ ID NO: 2), E (SEQ ID NO: 5) and G (SEQ ID NO: 7) produced rapid increases in bowel activity as measured by colorectal pressure manometry.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference.

REFERENCES

Altamura M, *Expert Opin Ther Pat.* 2012; 22(1):57-77
Bang R, Sass G, Kiemer A K, Vollmar A M, Neuhuber W L, Tiegs G (2003). Neurokinin-1 receptor antagonists CP-96, 345 and L-733,060 protect mice from cytokine-mediated liver injury. J. Pharmacol. Exp. Ther. 305: 31-39
Bowden J J, Baluk P, Lefevre P M, Vigna S R, McDonald D M (1996). Substance P (NK1) receptor immunoreactivity on endothelial cells of the rat tracheal mucosa. Am. J. Physiol, 270: L404-414
Burcher E, Shang F, Warner F J, Du Q, Lubowski D Z, King D W, Liu L (2008). Tachykinin NK2 receptor and functional mechanisms in human colon: changes with indomethacin and in diverticular disease and ulcerative colitis. J. Pharmacol. Exp. Ther. 324: 170-178
Carini F, Lecci A, Tramontana M, Giuliani S, Maggi C A (2001). Tachykinin NK(2) receptors and enhancement of cholinergic transmission in the inflamed rat colon: an in vivo motility study. Br. J. Pharmacol. 133: 1107-1113
Cialdai C, et al., *Eur J Pharmacol.* 2006; 549(1-3):140-8
Drury D E, Chong L K, Ghahramani P, Peachell P T (1998). Influence of receptor reserve on beta-adrenoceptor-mediated responses in human lung mast cells. Br. J. Pharmacol. 124: 711-718
Feldman P D (1995). Neurokinin 1 receptor mediation of the vasodepressor effects of Substance P in the nucleus of the tractus solitarius. J. Pharmacol. Exp. Therap. 273: 617-623 Hall J M, Flowers J M, Morton I K (1992). A pharmacological study of NK1 and NK2 tachykinin receptor characteristics in the rat isolated urinary bladder. Br. J. Pharmacol. 107: 777-784
Hastrup H, Schwartz T W (1996). Septide and Neurokinin A are high-affinity ligands on the NK-1 receptor: evidence from homologous versus heterologous binding analysis. FEBS Letts 399: 264-266
Hughes M (2014). Bowel management in spinal cord injury patients. Clin. Colon Rect. Surg. 27: 113-115

Jafri M S, Weinreich D (1996). Substance P hyperpolarizes vagal sensory neurones of the ferret. J. Physiol. 493: 157-166

Kaczynska K, Jampolsky M, Szereda-Prize Staszewska M (2016). The role of vagal pathway and NK1 and NK2 receptors in cardiovascular and respiratory effects of neurokinin A. Clin. Exp. Pharmacol. Physiol. 43: 818-824

Kudlacz E M et al., J Pharmacol Exp Ther. 1996; 279(2): 732-9

Lee J S, Kim S W, Tee S H, Kim J C, Choi T B, Cho S Y, Kim J H, Korea Spinal Cord Injury Association (2016). Factors affecting quality of life among spinal cord injury patients in Korea. Neurourol. J. 20: 316-320

March, J, Advanced Organic Chemistry: Reactions, Mechanisms and Structure, 4th Ed. (New York: Wiley-Interscience, 1992

McElroy A B, et al., *J Med Chem.* 1992; 35(14):2582-91

Miike T, Shirahase H, Kanda M, Kunishiro K, Kurahashi K (2009). NK1 receptor-mediated endothelium-dependent relaxation and contraction with different sensitivity to post-receptor signaling in pulmonary arteries. Vascul. Pharmacol. 51: 147-153

Mule F, D'Angelo S, Tabacchi G, Serio R (2000). Involvement of tachykinin NK2 receptors in the modulation of spontaneous motility in rat proximal colon. Neurogastroenterol. Motil. 12: 459-466

Mussap C J, Stamatakos C, Bracher E (1996). Radioligand binding, autoradiographic and functional studies demonstrate tachykinin NK-2 receptors in dog urinary bladder. J. Pharmacol. Exp. Therap. 279: 423-434

Oriowo M A, Bevan T A, Bevan R D (1989). Variation in sensitivity of six cat and six rat arteries to norepinephrine can be related to differences in agonist affinity and receptor reserve. J. Pharmacol. Exp. Titer, 251: 16-20

Parlani M, Conte B, Cirillo R, Manzini S (1996). Characterization of tachykinin NK2 receptor on dog proximal colon. Antagonism by MEN 10,627 and SR 48,968. Eur. J. Pharmacol. 318: 419-424

Quartara et al., *Med Res Rev.* 1995; 15(2):139-55 (Review)

Ricciardolo F L, Trevisani M, Geppetti P, Nadel J A, Amadesi S, Bertrand. C (2000). Role of nitric oxide and septide-insensitive NK(1) receptors in bronchoconstriction induced by aerosolised Neurokinin A in guinea-pigs. Br. J. Pharmacol. 129: 915-920

Sagan S, Chassaing G, Pradier L, Lavielle S (1996). Tachykinin peptides affect differently the second messenger pathways after binding to CHO-expressed human NK-1 receptors. J. Pharmacol. Exp. Therap. 276: 1039-1048

Singh R, Rohilla R K, Sangwan K, Siwach R, Magu N K, Sangwan S S (2011). Bladder management methods and urological complications in spinal cord injury patients. Ind. J. Orthop. 45: 141-147

Torrens Y, Beaujouan J C, Saffroy M, Glowinski J (2000). Further evidence for the presence of "septide-sensitive" tachykinin binding sites in tissues possessing solely NK(1) tachykinin receptors. Biochem. Biophys. Res. Commun. 270: 668-772 van Koeveringe G A, Vahabi B, Andersson K E, Kirschner-Herrmans R, Oelke M (2011) Detrusor underactivity: a plea for new approaches to a common bladder dysfunction. Neurourol. Urodyn. 30: 723-728

Wang Y, Wang D H (2012). Role of Substance P in renal injury during DOCA-salt hypertension. Endocrinology 153: 5972-5979

Warner F J, Miller R C, Burcher E (2002). Structure-activity relationship of neurokinin A(4-10) at the human tachykinin NK(2) receptor: the effect of amino acid substitutions on receptor affinity and function. Biochem. Pharmacol. 63: 2181-2186

Warner F J, Miller R C, Burcher F (2003). Human tachykinin NK2 receptor: a comparative study of the colon and urinary bladder. Clin. Exp. Pharmacol. Physiol. 30: 632-629

Yang Y, Yan M, Zhang H, Wang X (2013). Substance P participates in immune-mediated hepatic injury induced by concanavalin A in mice and stimulates cytokine synthesis in Kupffer cells. Exp. Ther. Med. 6: 459-464

Yilmaz B, Akkoç Y, Alaca R, Erhan B, Gündüz B, Yfldiz N, Gök H, Köklü K, Cinar E, Alerridaroğlu Ersöz M, Kampolat H, Denmir Y, Bardak A N, Turna I, Catalbaş N, Güneş S, Tunç H. (2014) Intermittent catheterization in patients with traumatic spinal cord injury: obstacles, worries, level of satisfaction. Spinal Cord 52: 826-830

One skilled in the art will readily appreciate that the presently described subject matter is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

That which is claimed:

1. A synthetic peptide selected from the group consisting of:
   the amino acid sequence Asp-Arg-Phe-Val-Gly-(NMe-Leu)-Nle-NH2 (SEQ ID NO: 2);
   the amino acid sequence Asp-Lys-Phe-Val-(β-Ala)-Leu-Nle-NH2 (SEQ ID NO: 7);
   the amino acid sequence Asp-Lys-Phe-Val-(β-Ala)-Leu-Met-NH2 (SEQ ID NO: 5;
   the amino acid sequence Asp-Arg-Phe-Val-(β-Ala)-Leu-Nle-NH2 (SEQ ID NO: 11);
   the amino acid sequence Asp-Arg-Phe-Val-Gly-(NMe-Leu)-Met-NH2 (SEQ ID NO: 3); and
   the amino acid sequence Asp-Arg-Phe-Val-(β-Ala)-Leu-Met-NH2 (SEQ ID NO: 9).

2. A pharmaceutical composition comprising a peptide according to claim 1, or a pharmaceutically acceptable salt thereof, and a pharmaceutically acceptable excipient.

3. A pharmaceutical composition comprising a peptide according to claim 1 selected from the group consisting of SEQ ID NOs: 2 and 3, or a pharmaceutically acceptable salt thereof, in a formulation beneficial for a hydrophilic active ingredient.

4. A pharmaceutical composition comprising a peptide according to claim 1 selected from the group consisting of SEQ ID NOs: 5, 7, and 11, or a pharmaceutically acceptable salt thereof, in a formulation beneficial for a hydrophobic active ingredient.

5. A pharmaceutical composition comprising a peptide according to claim 1 selected from the group consisting of SEQ ID NOs: 2, 7, and 11, or a pharmaceutically acceptable salt thereof, and a pharmaceutically acceptable excipient.

6. A method for inducing one or both of urinary voiding and defecation in a mammal, which comprises administering on an as-needed basis to the mammal a therapeutically effective amount of a composition comprising a peptide selected from the group consisting of SEQ ID NOs: 2, 3, 5, 7, 9, and 11, or a pharmaceutically acceptable salt thereof, to induce the as-needed one or both of urinary voiding and defecation.

7. The method of claim 6, wherein the composition comprises the peptide selected from the group consisting of SEQ ID NOs: 2 and 3 in a formulation beneficial for a hydrophilic active ingredient.

8. The method of claim 6, wherein the composition comprises the peptide selected from the group consisting of SEQ ID NOs: 5, 7 and 11 in a formulation beneficial for a hydrophobic active ingredient.

9. The method of claim 6 wherein the composition comprises the peptide selected from the group consisting of SEQ ID NOs: 2, 7 and 11.

10. The method of claim 6, wherein the composition is formulated as an immediate release dosage form.

11. The method of claim 6, wherein the administering is one or a combination of parenteral, intravenous, topical, transdermal, intramuscular, subcutaneous, transnasal, inhalation, transrectal, lingual, sublingual, transmucosal, buccal, and transbuccal.

12. The method of claim 6, wherein the administering is intraorally.

13. The method of claim 6, wherein the mammal has a voiding and/or defecation dysfunction as a result of one of spinal cord injury, traumatic brain injury, multiple sclerosis, spina bifida, degenerative brain disease, Alzheimer's, Parkinson's, dementia, diabetes, advanced age, postoperative status, and combinations thereof.

14. The method of claim 6, wherein the mammal is a human, an animal, a cat, a dog, a horse, a cow, a pig, or a sheep.

15. The method of claim 6, wherein the as-needed administering ranges from about 1 minute to about 10 minutes prior to when the voiding and/or defecation is desired.

16. The method of claim 6, wherein the therapeutically effective amount of the composition is in a dosage form comprising at least one of a rapidly disintegrating matrix or a bioerodible polymeric carrier.

17. A method for preparing a peptide selected from the group consisting of SEQ ID NOs: 2, 3, 5, 7, 9, and 11, the method comprising:
chemically synthesizing a peptide comprising the amino acid sequence of a peptide selected from the group consisting of SEQ ID NOs: 2, 3, 5, 7, 9, and 11; and
purifying the peptide.

18. The method of claim 17, wherein the chemical synthesis step comprises solid phase chemical synthesis.

19. The method of claim 17, wherein the purification step comprises reverse phase chromatography.

* * * * *